United States Patent [19]

Zimmermann

[11] Patent Number: 5,728,708
[45] Date of Patent: Mar. 17, 1998

[54] PHARMACOLOGICALLY ACTIVE PYRIDINE DERIVATIVES AND PROCESSES FOR THE PREPARATION THEREOF

[75] Inventor: Jürg Zimmermann, Wallbach, Switzerland

[73] Assignee: Novartis Corporation, Summit, N.J.

[21] Appl. No.: 446,743

[22] PCT Filed: Sep. 21, 1994

[86] PCT No.: PCT/EP94/03151

§ 371 Date: May 31, 1995

§ 102(e) Date: May 31, 1995

[87] PCT Pub. No.: WO95/09853

PCT Pub. Date: Apr. 13, 1993

[30] Foreign Application Priority Data

Oct. 1, 1993 [CH] Switzerland .............. 2969/93
Jul. 18, 1994 [CH] Switzerland .............. 2281/94

[51] Int. Cl.⁶ .............. C07D 401/04; C07D 401/14; A61K 31/505
[52] U.S. Cl. .............. 514/275; 514/252; 514/235.8; 514/86; 544/295; 544/122; 544/331; 544/243
[58] Field of Search .............. 514/275, 252, 514/235.8, 86; 544/295, 243

[56] References Cited

U.S. PATENT DOCUMENTS 4,725,600  2/1988  Takaya et al. .............. 514/269
4,966,622  10/1990  Rempfler et al. .............. 71/92
5,159,078  10/1992  Rempfler et al. .............. 544/330

FOREIGN PATENT DOCUMENTS

| 0164204 | 12/1985 | European Pat. Off. |
| 0233461 | 8/1987 | European Pat. Off. |
| 337943 | 10/1989 | European Pat. Off. |
| 388838 | 9/1990 | European Pat. Off. |
| 564409 | 10/1993 | European Pat. Off. |
| 588762 | 3/1994 | European Pat. Off. |
| 3436380 | 4/1986 | Germany . |

*Primary Examiner*—John M. Ford
*Attorney, Agent, or Firm*—Gregory D. Ferraro

[57] ABSTRACT

N-phenyl-2-pyrimidineamine derivatives of formula I

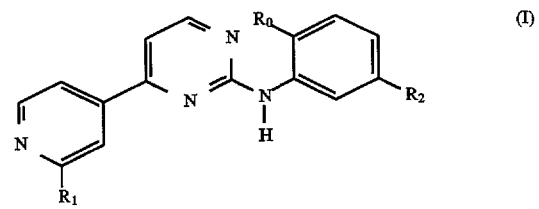

wherein the substituents are as defined in claim 1 and the derivatives of formula I can be used, for example, in the treatment of tumour diseases.

23 Claims, No Drawings

PHARMACOLOGICALLY ACTIVE PYRIDINE DERIVATIVES AND PROCESSES FOR THE PREPARATION THEREOF

This application is filed under 35 U.S.C. §371 as a national phase application of PCT/EP94/03148, filed Sep. 21, 1994.

The invention relates to N-phenyl-4-(4-pyridyl)2-pyrimidineamine derivatives, to processes for the preparation thereof, to medicaments comprising those compounds, and to the use thereof in the preparation of pharmaceutical compositions for the therapeutic treatment of warm-blooded animals.

The invention relates to N-phenyl2-pyrimidineamine derivatives of formula I

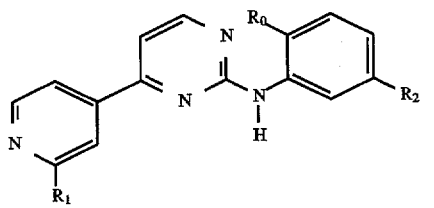

wherein
$R_0$ is hydrogen, halogen, lower alkoxy or lower alkyl,
$R_1$ is
 a) N-(amino-lower alkyl)-carbamoyl,
 b) N-(hydroxy-lower alkyl)-carbamoyl,
 c) hydrazino,
 d) cyclohexyl-amino that is unsubstituted or substituted by amino,
 e) piperazinyl that is unsubstituted or substituted by amino-lower alkyl,
 f) morpholinyl, or
 g) lower alkylamino that is substituted by morpholinyl, hydroxy-lower alkylamino, cyano, imidazolyl, guanidyl, amino, lower alkanoylamino, lower alkylamino-carbonylamino, amidino, di-lower alkylamino-cyclohexyl, carboxy, lower alkoxycarbonyl, carbamoyl, N-hydroxy-carbamoyl, hydroxy, lower alkoxy, dihydroxyphosphoryloxy, piperazinyl, lower alkanoyl-piperazinyl, formylpiperazinyl, prolylamido or by a radical of the formula $H_2N$—$CH(R)$—$C(=O)$—NH— wherein R is hydrogen, $C_1$–$C_4$alkyl, benzyl, hydroxymethyl, 1-hydroxy-ethyl, mercaptomethyl, 2-methylthio-ethyl, indol-3-yl-methyl, phenyl-methyl, 4-hydroxy-phenyl-methyl, carbamoyl-methyl, 2-carbamoyl-ethyl, carboxy-methyl, 2-carboxy-ethyl, 4-amino-butyl, 3-guanidyl-propyl or R is 1H-imidazol-4-yl-methyl, and $R_2$ is $C_1$–$C_6$alkyl, $C_1$–$C_3$alkoxy, chlorine, bromine, iodine, trifluoromethyl, hydroxy, phenyl, amino, mono($C_1$–$C_3$alkyl)amino, di($C_1$–$C_3$alkyl)amino, $C_2$–$C_4$alkanoyl, propenyloxy, carboxy, carboxy-methoxy, ethoxycarbonyl-methoxy, sulfanilamido, N,N-di-($C_1$–$C_3$alkyl) sulfanilamido, N-methyl-piperazinyl, piperidinyl, 1H-imidazol-1-yl, 1H-triazol-1-yl, 1H-benzimidazol-2-yl, 1-naphthyl, cyclopentyl, 3,4-dimethyl-benzyl or a radical of one of the formulae:
—$CO_2R_3$, —NH—C(=O)—$R_3$, —N($R_3$)—C(=O)—$R_4$, —O—$(CH_2)_n$—N($R_3$)—$R_4$,
—C(=O)—NH—$(CH_2)_n$—$R_4^a$, —C(=O)—NH—$(CH_2)_n$—N($R_3$)—$R_4$, —CH($CH_3$)—NH—CHO,
—C($CH_3$)=N—OH, —C($CH_3$)=N—O—$CH_3$, —CH($CH_3$) —$NH_2$, —NH—$CH_2$—C(=O)—N($R_3$)—$R_4$,

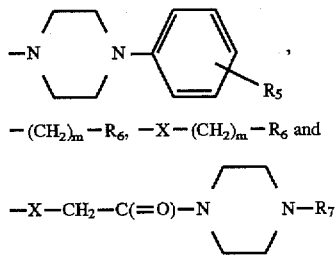

—$(CH_2)_m$—$R_6$, —X—$(CH_2)_m$—$R_6$ and

—X—$CH_2$—C(=O)—N⟨ ⟩N—$R_7$ wherein $R_3$ and $R_4$ are each independently of the other $C_1$–$C_3$alkyl, $R_4^a$ is hydroxy, amino or imidazolyl, X is oxygen or sulfur, m is 1, 2 or 3, n is 2 or 3, $R_5$ is hydrogen, $C_1$–$C_3$alkyl, $C_1$–$C_3$alkoxy, chlorine, bromine, iodine or trifluoromethyl, $R_6$ is 1H-imidazol-1-yl or morpholinyl and $R_7$ is $C_1$–$C_3$alkyl or is phenyl that is unsubstituted or mono-substituted by $C_1$–$C_3$alkyl, halogen or by trifluoromethyl, and the salts thereof.

Halogen $R_0$ is fluorine, bromine, iodine or preferably chlorine.

Lower alkoxy $R_0$ is preferably methoxy.

Lower alkyl $R_0$ is preferably methyl.

Amino-lower alkyl in a radical $R_1$ is preferably ω-amino-$C_2$–$C_3$alkyl.

Hydroxy-lower alkyl in a radical $R_1$ is preferably ω-hydroxy-$C_2$–$C_3$alkyl.

Cyclohexyl-amino $R_1$ substituted by amino is preferably 4-amino-cyclohexyl-amino. Di-lower alkylamino-cyclohexyl as part of a substituted lower alkyl radical $R_1$ is preferably 4-di-lower alkylamino-cyclohexyl, preferably 4-dimethylamino-cyclohexyl.

Piperazinyl $R_1$ is preferably 1-piperazinyl. Piperazinyl $R_1$ substituted by amino-lower alkyl is preferably 4-(2-aminoethyl)-piperazin-1-yl.

Morpholinyl $R_1$ and morpholinyl in a radical $R_1$ are preferably 4-morpholinyl, wherein the free valency extends from the nitrogen. Lower alkylamino $R_1$ substituted by morpholinyl is preferably 2-morpholin-4-yl-ethylamino.

Hydroxy-lower alkylamino in a radical $R_1$ is preferably 2-hydroxy-ethylamino. Lower alkylamino substituted by hydroxy-lower alkylamino is preferably 3-(2-hydroxy-ethyl-amino)-prop-1-ylamino.

Imidazolyl $R_4^a$ in a radical $R_2$ is preferably 1H-imidazol-4-yl.

Lower alkanoylamino in a radical $R_1$ is preferably acetylamino.

Lower alkylamino-carbonylamino in a radical $R_1$ is preferably methylamino-carbonyl-amino.

Di-lower alkylamino in a radical $R_1$ is preferably dimethylamino.

Formyl-piperazinyl in a radical $R_1$ is preferably 4-formyl-piperazinyl.

Lower alkylamino $R_1$ substituted by cyano, imidazolyl, guanidyl, amino, lower alkanoyl-amino, lower alkylamino-carbonylamino, amidino, di-lower alkylamino-cyclohexyl, carboxy, lower alkoxycarbonyl, carbamoyl, N-hydroxy-carbamoyl, hydroxy, lower alkoxy, dihydroxyphosphoryloxy, piperazinyl, lower alkanoyl-piperazinyl, formylpiperazinyl, prolylamido or by a radical of the formula $H_2N$—$CH(R)$—$C(=O)$—NH— is preferably di- or tri-methylamino substituted by those substituents, the substituents preferably being in the ω-position. Lower alkyl $R_1$ substituted by hydroxy can preferably also be 2-hydroxy-propyl.

A radical of the formula $H_2N$—$CH(R)$—$C(=O)$—, wherein R is as defined above, is preferably the acyl radical of any one of the following amino acids which regularly occur in proteins: glycine, alanine, valine, leucine, isoleucine, phenylalanine, serine, threonine, cysteine, methionine, tryptophan, tyrosine, asparagine, glutamine, aspartic acid, glutamic acid, lysine, arginine and histidine, especially in their naturally occurring configuration, preferably the (L)-configuration.

Within the scope of this text, the term "lower" denotes radicals having up to and including 7, preferably up to and including 4, carbon atoms.

Unless otherwise indicated in the context concerned, lower alkyl is preferably methyl or ethyl.

The compounds of formula I can form acid addition salts, for example with inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid, oxalic acid or amino acids, such as arginine or lysine, aromatic carboxylic acids, such as benzoic acid, 2-phenoxy-benzoic acid, 2-acetoxy-benzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxy-ethane-sulfonic acid, or aromatic sulfonic acids, for example benzene-, p-toluene- or naphthalene-2-sulfonic acid. Mono, di- or, if other basic groups, such as amino or guanidyl groups, are present in the radical $R_1$, poly-acid addition salts can be formed.

Compounds of formula I having acidic groups, for example a free carboxy group in the radical $R_1$, can form metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethyl-piperazine.

Compounds of formula I that possess both acidic and basic groups can form internal salts.

For the purpose of isolation or purification and also in the case of the compounds used further as intermediates, it is also possible to use pharmaceutically unacceptable salts. Only the pharmaceutically acceptable non-toxic salts are used therapeutically, however, and those are therefore preferred.

In view of the close relationship between the novel compounds in free form and in the form of their salts, including also salts that can be used as intermediates, for example in the purification of the novel compounds or in order to identify those compounds, herein-before and hereinafter any reference to the free compounds is to be understood as including also the corresponding salts, where appropriate and expedient.

The compounds of formula I exhibit valuable pharmacological properties: for example, they inhibit the enzyme protein kinase C with a high degree of selectivity. Phospholipid-and calcium-dependent protein kinase C occurs in cells in a number of forms and participates in various fundamental processes, such as signal transmission, proliferation and differentiation, and also the release of hormones and neurotransmitters. The activation of that enzyme is effected either by receptor-mediated hydrolysis of phospholipids of the cell membrane or by direct interaction with certain tumour-promoting active substances. The sensitivity of the cell to receptor-mediated signal transmission can be substantially influenced by modifying the activity of protein kinase C (as a signal transmitter). Compounds that are capable of influencing the activity of protein kinase C can be used as tumour-inhibiting, antiinflammatory, immunomodulating and antibacterial active ingredients and may even be of value as agents against atherosclerosis and disorders of the cardiovascular system and central nervous system.

Formerly, porcine brain protein kinase C purified in accordance with the procedure described by T. Uchida and C. R. Filburn in J. Biol. Chem. 259, 12311–4 (1984) was used to determine the inhibitory action on protein kine C, and the inhibitory action on protein kinase C was determined in accordance with the procedure of D. Fabbro et al., Arch. Biochem. Biophys. 239, 102–111 (1985).

The porcine brain protein kinase C formerly used is a mixture of various sub-types (isotypes) of protein kinase C. If pure recombinant isotypes are used instead of porcine brain protein kinase C in the above test it is found that the compounds of formula I inhibit the "conventional" isotype α preferentially whereas the other "conventional" isotypes β-1, β-2 and γ and especially the "non-conventional" isotypes δ, ε and η and the "atypical" isoform ζ are generally inhibited to a lesser extent and in some cases hardly at all.

Recombinant PKC isotypes are cloned, expressed and purified in the following manner:

The production of various proteins with the aid of baculoviruses, and their cloning and isolation from Sf9 insect cells are carried out as described by M. D. Summers and G. E. Smith, "A manual method for baculovirus vectors and insect cell culture procedure", Texas Agricul. Exptl. Station Bull. (1987), 1555. The construction and isolation of recombinant viruses for the expression of PKC-α (bovine), PKC-β1 (human), PKC-β2 (human) and PKC-γ (human/bovine hybrid) in Sf9 cells are effected in the manner described by Stabel et al. [S. Stabel, M. Liyanage and D. Frith, "Expression of protein kinase C isozymes in insect cells and isolation of recombinant proteins", Meth. Neurosc. (1993)]. The production of the PKC isotypes in Sf9 cells is carried out in the manner indicated by Stabel et al. (see above), and the purification of the enzymes is effected in accordance with the method described in the publication by McGlynn et al. [E. McGlynn, J. Liebetanz, S. Reutener, J. Wood, N. B. Lydon, H. Hofstetter, M. Vanek, T. Meyer and D. Fabbro, "Expression and partial characterization of rat protein kinase C-δ and protein kinase C-ζ in insect cells using recombinant baculovirus", J. Cell. Biochem. 49, 239–250 (1992)]. For the generation of recombinant PKC-δ (rat), PKC-ε (rat), PKC-ζ (rat) and PKC-η (mouse), and their expression and purification, the procedure described by Liyanage et al. ["Protein kinase C group B members PKC-δ, -ε, -ζ and PKC-λ: Comparison of properties of recombinant proteins in vitro and in vivo", Biochem. J. 283, 781–787 (1992)] and McGlynn et al., respectively, (see above) is followed, with the additional feature that the transfer vector pAc360 is used for the expression of PKC-η [V. Luckow and M. D. Summers, "Trends in the development of baculovirus expression", Biotechnology 6, 47–55 (1988)].

The measurement of the activity of the recombinant PKC isotypes obtained by the above method is carried out in the absence of lipid and calcium (co-factors). Protamine sulfate phosphorylated in the absence of co-factors is used as the substrate. The activity of the enzymes reflects the transfer of $^{32}P$ from $\gamma$-[$^{32}P$]-ATP to protamine sulfate. Protamine sulfate is a mixture of polypeptides each comprising four C-terminal arginine residues. Phosphate incorporation is measured under the following conditions: 100 µl of the reaction mixture contain in final concentrations 20 mM TRIS-HCl pH 7.4, 10 mM Mg[NO$_3$]$_2$, 0.5 mg/ml of protamine sulfate, 10 µM ATP (0.1 µCi γ-[$^{32}$P]-ATP; 10 Ci/mol; Amersham, Little Chalfont, United Kingdom), various concentrations of the inhibitory compounds and 0.5–2.5 U (units: a unit is the amount of enzyme that, in one minute and per milligram of protein, transfers one nanomole of $^{32}$P from the above-mentioned γ-[$^{32}$P]-ATP to histone H1 [Sigma, type V-S]) of the enzymes. The reaction is started by the addition of the enzymes and transfer at 32° C. The reaction time is 20 minutes. The reaction is then stopped by dripping aliquots of 50 µl onto P81 chromatography paper (Whatman, Maidstone, United Kingdom). After removing unbound γ-[$^{32}$P]-ATP and nucleotide fragments by washing operations as described by J. J. Witt and R. Roskoski, "Rapid protein kinase assay using phospho-cellulose-paper absorption", Anal. Biochem. 66, 253–258 (1975), the substrate phosphorylation is determined by scintillation measurement. In that test, the compounds of formula I inhibit the α-isotype of protein kinase C (PKC) at an IC$_{50}$ of as low as approximately from 0.1 to 5.0 µmol/litre, generally approximately from 0.1 to 1.0 µmol/litre. In contrast, the other isotypes of PKC are generally inhibited only at distinctly higher concentrations (i.e. at concentrations up to more than 300 times higher).

As may be expected purely on the basis of the above-described inhibitory action on protein kinase C, the compounds of formula I exhibit antiproliferative properties which can be demonstrated directly in another test described in the following in which the inhibitory action of the compounds of formula I on the growth of human T24 bladder carcinoma cells is determined. Those cells are incubated in Eagle's minimal essential medium, to which 5% (v/v) fetal calf serum has been added, in a humidified incubator at 37° C. and with 5% by volume of CO$_2$ in the air. The carcinoma cells (1000–1500) are sown in 96-well microtitre plates and incubated overnight under the above-mentioned conditions. The test compound is added in serial dilutions on day 1. The plates are incubated for 5 days under the above-mentioned conditions. During that period the control cultures undergo at least four cell divisions. After incubation, the cells are fixed with 3.3% (w/v) aqueous glutaraldehyde solution, washed with water and stained with 0.05% (weight/volume) aqueous methylene blue solution. After washing, the dye is eluted with 3% (w/v) aqueous hydrochloric acid. The optical density (OD) per well, which is directly proportional to the number of cells, is then measured at 665 nm using a photometer (Titertek multiskan). The IC$_{50}$ values are calculated with a computer system using the formula $$\frac{OD_{665}(\text{test}) \text{ minus } OD_{665}(\text{start})}{OD_{665}(\text{control}) \text{ minus } OD_{665}(\text{start})} \times 100.$$

The IC$_{50}$ values are defined as being the concentration of active ingredient at which the number of cells per well at the end of the incubation period is only 50% of the number of cells in the control cultures. In the case of the compounds of formula I, the IC$_{50}$ values so ascertained are approximately from 0.01 to 10 µmol/litre, generally approximately from 0.01 to 1 µmol/litre.

The anti-tumour activity of the compounds of formula I can also be demonstrated in vivo:

Female Balb/c hairless mice with s.c. transplanted human bladder tumours T24 are used to determine the anti-tumour activity. On day 0, with the animals under peroral forene narcosis, approximately 25 mg of a solid tumour are placed under the skin on the animals' left flank and the small incised wound is closed by means of suture clips. On day 6 after the transplantation, the mice are divided at random into groups of 6 animals and treatment commences. The treatment is carried out for 15 days with peroral or intraperitoneal administration once daily of a compound of formula I in dimethyl sulfoxide/Tween 80/-sodium chloride solution in the various doses. The tumours are measured twice a week with a slide gauge and the volume of the tumours is calculated. In that test, the peroral or intraperitoneal administration of a compound of formula I brings about a marked reduction in the average tumour volume in comparison with the untreated control animals.

On the basis of the properties described, the compounds of formula I can be used especially as tumour-inhibiting active ingredients, for example in the treatment of tumours of the bladder and the skin. When the compounds of formula I are used in the treatment of cancer in combination with other chemotherapeutic drugs, they prevent the development of resistance (multidrug resistance) or eliminate an already existing resistance to the other chemotherapeutic drugs. They are also suitable for the other uses mentioned above for protein kinase C modulators and can be used especially in the treatment of disorders responsive to inhibition of protein kinase C.

Some of the compounds of formula I also inhibit the tyrosine kinase activity of the receptor for the epidermal growth factor (EGF). That receptor-specific enzyme activity plays a key role in signal transmission in a large number of mammalian cells, including human cells, especially epithelial cells, cells of the immune system and cells of the central and peripheral nervous system. In the case of various types of cell, the EGF-induced activation of the receptor-associated tyrosine protein kinase (EGF-R-TPK) is a prerequisite for cell division and accordingly for the proliferation of a cell population. The addition of EGF-receptor-specific tyrosine kinase inhibitors thus inhibits the replication of those cells.

Inhibition of EGF-receptor-specific tyrosine protein kinase (EGF-R-TPK) can be demonstrated, for example, using the method of E. McGlynn et at., Europ. J. Biochem. 207, 265–275 (1992). The compounds according to the invention inhibit the enzyme activity by 50% (IC50) for example at a concentration of from 0.1 to 10 µM.

The compounds of formula I that inhibit the tyrosine kinase activity of the receptor for the epidermal growth factor (EGF) can accordingly be used, for example, in the treatment of benign or malignant tumours. They are able to bring about tumour regression and to prevent metastatic spread and the growth of micrometastases. They can be used especially in the case of epidermal hyperproliferation (psoriasis), in the treatment of neoplasia of epithelial character, for example mastocarcinoma, and in the case of leukaemia. The compounds can also be used in the treatment of disorders of the immune system and inflammation if protein kinases are involved. Furthermore, those compounds of formula I can be used in the treatment of disorders of the central or peripheral nervous system if signal transmission by protein kinases is involved.

The compounds of formula I and the salts thereof also inhibit the enzyme p34$^{cdc2}$/cycline B$^{cdc13}$ kinase. That kinase controls, in addition to other cdc2-related kinases, specific phases of cell division, especially the transition from the G$_1$-phase to the S-phase and more especially the transition from the G$_2$-phase to the M-phase.

In chronological order, the cycle of a eukaryotic cell consists of the interphase and the M-phase. The interphase is accompanied by an increase in the size of the cell. In chrono-logical order, the interphase consists for its part of the $G_1$-phase, the S-phase and the $G_2$-phase. In the $G_1$-phase (G=gap) biosynthetic processes take place in the cell. In the S-phase (synthesis phase) the DNA doubles. The cell then enters the $G_2$-phase which ends with the commencement of mitosis.

In chronological order, the M-phase for its part consists of the division of the cell nucleus (mitosis) and the division of the cytoplasm (cytokinesis).

The above-mentioned inhibition of the enzyme $p34^{cdc2}$/cycline $B^{cdc13}$ kinase can be demonstrated by the following test:

10 μM 1-methyl-adenine are used to induce starfish oocytes to enter the M-phase. The oocytes are then frozen in liquid nitrogen and stored at −80° C. If necessary, the oocytes are homogenised and centrifuged, as described in D. Arion et al., Cell 55,371–378 (1988) and V. Rialet and L. Meijer, Anticancer Res. 11, 1581–1590 (1991). In order to purify the $p34^{cdc2}$/cycline $B^{cdc13}$ kinase, the supernatant of the oocytes is added to $p9^{CKShs}$-Sepharose grains prepared from recombinant human protein $p9^{CKShs}$, as described in L. Azzi et al., Eur. J. Biochem. 203, 353–360 (1992). After 30 minutes at 4° C. while being turned constantly, the grains are washed thoroughly and the active $p34^{cdc2}$/cycline $B^{cdc13}$ kinase is eluted with free protein $p9^{CKShs}$ (3 mg/ml). The eluted kinase is tested using histone $H_1$ as substrate, as described in L. Meijer et at., EMBO J. 8, 2275–2282 (1989) and EMBO J. 10, 1545–1554 (1991). In that test, the compounds of formula I and their salts exhibit an inhibiting concentration $IC_{50}$ [μmol/litre] of approximately from 0.0005 to 2, in most cases approximately from 0.001 to 0.4.

That finding would also lead to the expectation that the compounds of formula I and the salts thereof can be used in the treatment of hyperproliferative disorders, such as tumours and psoriasis.

The compounds of formula I also inhibit the production of HIV viruses, as shown by the test below, and can accordingly be used as agents against the immune deficiency disease AIDS. The initial symptoms observed after HIV infection in humans is followed by a clinical latency period which can last several years. After that period, the stage known as AIDS occurs and usually progresses to death. The latency period is attributed to several factors: immune response, occlusion of the viruses in lymph nodes or other tissue and entry into a stage of molecular and viral latency in which the infected cells do not complete the vital cell cycle, which is why infectious viruses cannot be produced and the infection cannot spread. That stage of molecular latency has been investigated using cell models, such as the ACH-2 cell line [K. Clouse et al., J. Immunol. 142, 431 (1989)] and the U1 cell line [T. Folks et al., J. Immunol. 140, 117 (1988)]. Those cells are infected with HIV-1 viruses, but have only a low content of infectious viruses. If, however, those cells are stimulated with physiologically relevant factors that are known to be increased in AIDS patients, such as tumour necrosis factor, interleukin-6 etc., or with chemical inductors, such as phorbol diesters, for example 13-O-acetyl-12-O-n-tetradecanoyl-phorbol, a massive production of virus follows. The ACH-2 and U 1 cells are representatives of two different cell families that are targets for HIV infection, namely lymphocytes and macro-phages.

Hitherto, effective prevention of the progression of HIV infection to the outbreak of AIDS has not been possible. Many attempts have been made to prevent virus replication after the outbreak of AIDS, that is to say, in a stage in which viruses are produced on a massive scale. In contrast, the compounds of formula I interfere with cell processes that lead to the activation of latently infected HIV cells without impairing normal cell processes, such as cell division.

If the above-mentioned U1 or ACH-2 cells are used as a model for viral latency, it can be demonstrated that HIV virus production induced by 13-O-acetyl-12-O-n-tetradecanoylphorbol or tumour necrosis factor-alpha are effectively inhibited by the compounds of formula I at a concentration of approximately from 0.001 to 1 μmol/litre, for example at 0.03 μmol/litre.

Preferred are compounds of formula Ia

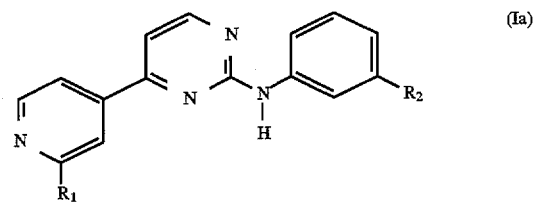

(Ia)

wherein $R_1$ is
a) N-(amino-lower alkyl)-carbamoyl,
b) N-(hydroxy-lower alkyl)-carbamoyl,
c) hydrazino,
d) cyclohexyl-amino that is unsubstituted or substituted by amino, or
e) lower alkylamino that is substituted by cyano, imidazolyl, guanidyl, amino, lower alkanoylamino, lower alkylamino-carbonylamino, amidino, di-lower alkylamino-cyclohexyl, carboxy, lower alkoxycarbonyl, carbamoyl, N-hydroxy-carbamoyl, hydroxy, lower alkoxy, dihydroxyphosphoryloxy, piperazinyl, lower alkanoyl-piperazinyl, formylpiperazinyl, prolylamido or by a radical of the formula $H_2N$—CH(R)—C(=O)—NH— wherein R is hydrogen, $C_1$–$C_4$alkyl, benzyl, hydroxymethyl, 1-hydroxy-ethyl, mercaptomethyl, 2-methylthio-ethyl, indol-3-yl-methyl, phenyl-methyl, 4-hydroxy-phenyl-methyl, carbamoyl-methyl, 2-carbamoyl-ethyl, carboxy-methyl, 2-carboxy-ethyl, 4-amino-butyl, 3-guanidyl-propyl or R is 1H-imidazol-4-yl-methyl, and $R_2$ is $C_1$–$C_6$alkyl, $C_1$–$C_3$alkoxy, chlorine, bromine, iodine, trifluoromethyl, hydroxy, phenyl, amino, mono ($C_1$–$C_3$alkyl)amino, di($C_1$–$C_3$alkyl)amino, $C_2$–$C_4$alkanoyl, propenyloxy, carboxy, carboxymethoxy, ethoxycarbonyl-methoxy, sulfanilamido, N,N-di($C_1$–$C_3$alkyl)sulfanilamido, N-methyl-piperazinyl, piperidinyl, 1H-imidazol-1-yl, 1H-triazol-1-yl, 1H-benzimidazol-2-yl, 1-naphthyl, cyclopentyl, 3,4-dimethyl-benzyl or a radical of one of the formulae:
—$CO_2R_3$, —NH—C(=O)—$R_3$, —N($R_3$)—C(=O)—$R_4$, —O—(CH$_2$)$_n$—N($R_3$)—$R_4$, —C(=O)—NH—(CH$_2$)$_n$—N($R_3$)—$R_4$, —CH(CH$_3$)—NH—CHO, —C(CH$_3$)=N—OH, —C(CH$_3$)=N—O—CH$_3$, —CH(CH$_3$)—NH$_2$, —NH—CH$_2$—C(=O)—N($R_3$)—$R_4$,

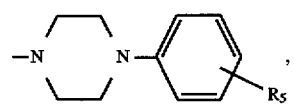

—(CH$_2$)$_m$—$R_6$, —X—(CH$_2$)$_m$—$R_6$ and

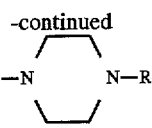

wherein $R_3$ and $R_4$ are each independently of the other $C_1$–$C_3$alkyl, X is oxygen or sulfur, m is 1, 2 or 3, n is 2 or 3, $R_5$ is hydrogen, $C_1$–$C_3$alkyl, $C_1$–$C_3$alkoxy, chlorine, bromine, iodine or trifluoromethyl, $R_6$ is 1H-imidazol-1-yl or morpholinyl and $R_7$ is $C_1$–$C_3$alkyl or is phenyl that is unsubstituted or mono-substituted by $C_1$–$C_3$alkyl, halogen or by trifluoromethyl, and the salts thereof.

A preferred group comprises compounds of formula I wherein $R_0$ is hydrogen, halogen, lower alkoxy or lower alkyl,
$R_1$ is
a) N-(amino-lower alkyl)-carbamoyl,
b) N-(hydroxy-lower alkyl)-carbamoyl,
c) hydrazino,
d) piperazinyl that is unsubstituted or substituted by amino-lower alkyl,
e) morpholinyl, or
f) lower alkylamino that is substituted by morpholinyl, hydroxy-lower alkylamino, imidazolyl, guanidyl, amino, lower alkanoylamino, lower alkylaminocarbonylamino, amidino, carboxy, lower alkoxycarbonyl, carbamoyl, N-hydroxy-carbamoyl, hydroxy, dihydroxyphosphoryloxy or by a radical of the formula $H_2N$—CH(R)—C(=O)—NH— wherein R is hydrogen, and
$R_2$ is chlorine, trifluoromethyl, carboxy, a radical of the formula —$CO_2R_3$ wherein $R_3$ is $C_1$–$C_3$alkyl, or a radical of the formula —C(=O)—NH—$(CH_2)_n$—$R_4^a$ wherein n is 2 or 3 and $R_4^a$ wherein n 2 or 3 and $R_4^a$ is hydroxy, amino or imidazolyl, and the salts thereof.

A further preferred group comprises compounds of formula I wherein $R_0$ is hydrogen,
$R_1$ is
a) N-(amino-lower alkyl)-carbamoyl,
b) N-(hydroxy-lower alkyl)-carbamoyl,
c) hydrazino or
d) lower alkylamino that is substituted by imidazolyl, guanidyl, amino, lower alkanoyl-amino, lower alkylamino-carbonylamino, amidino, carboxy, lower alkoxycarbonyl, carbamoyl, N-hydroxy-carbamoyl, hydroxy, dihydroxyphosphoryloxy or by a radical of the formula $H_2N$—CH(R)—C(=O)—NH— wherein R is hydrogen, and
$R_2$ is chlorine or trifluoromethyl, and the salts thereof.

Preferred are compounds of formula I wherein
$R_0$ is hydrogen, chlorine, lower alkyl or lower alkoxy,
$R_1$ is N-($\omega$-amino-$C_2$–$C_3$alkyl)-carbamoyl, N-($\omega$hydroxy-$C_2$–$C_3$alkyl)-carbamoyl, hydrazino, 2-hydroxy-propylamino or linear $C_2$–$C_3$alkylamino that is substituted in the $\omega$-position by morpholinyl, $\omega$-hydroxy-lower alkylamino, imidazolyl, guanidyl, amino, lower alkanoylamino, amidino, carboxy, lower alkoxycarbonyl, carbamoyl, N-hydroxycarbamoyl, hydroxy or by dihydroxyphosphoryloxy, and
$R_2$ is chlorine, trifluoromethyl, carboxy, a radical of the formula —$CO_2R_3$ wherein $R_3$ is $C_1$–$C_3$alkyl, or a radical of the formula —C(=O)—NH—$(CH_2)_n$—$R_4^a$ wherein n is 2 or 3 and $R_4^a$ is hydroxy, amino or imidazolyl, and the salts thereof.

Preferred are especially compounds of formula I wherein
$R_0$ is hydrogen,
$R_1$ is N-($\omega$-amino-$C_2$–$C_3$alkyl)-carbamoyl, N-($\omega$-hydroxy-$C_2$–$C_3$alkyl)-carbamoyl, hydrazino, 2-hydroxy-propylamino or linear $C_2$–$C_3$alkylamino that is substituted in the $\omega$-position by imidazolyl, guanidyl, amino, lower alkanoylamino, amidino, carboxy, lower alkoxycarbonyl, carbamoyl, N-hydroxy-carbamoyl, hydroxy or by dihydroxyphosphoryloxy, and
$R_2$ is chlorine or trifluoromethyl, and the salts thereof.

Especially preferred are compounds of formula I wherein
$R_0$ is hydrogen, chlorine, methyl or methoxy,
$R_1$ is N-($\omega$-amino-$C_2$–$C_3$alkyl)-carbamoyl, N-($\omega$-hydroxy-$C_2$–$C_3$alkyl)-carbamoyl, hydrazino, 2-hydroxy-propylamino or linear $C_2$–$C_3$alkylamino that is substituted in the $\omega$-position by 4-morpholinyl, $\omega$-hydroxy-ethylamino, 1H-imidazol-1-yl, 1H-imidazol-4-yl, guanidyl, amino, acetylamino, amidino, carboxy, ethoxycarbonyl, carbamoyl, N-hydroxycarbamoyl, hydroxy or dihydroxyphosphoryloxy, and
$R_2$ is chlorine, trifluoromethyl, carboxy, a radical of the formula —$CO_2R_3$ wherein $R_3$ is methyl, or a radical of the formula —C(=O)—NH—$(CH_2)_n$—$R_4^a$ wherein n is 2 or 3 and $R_4^a$ is hydroxy, amino or 1H-imidazol-4-yl, and the salts thereof.

More especially preferred are the compounds of formula I described in the Examples.

The compounds of formula I and the salts thereof are prepared in accordance with processes known per se. The process according to the invention for the preparation of an N-phenyl-2-pyrimidineamine derivative of formula I is effected as follows:

a) a compound of formula II

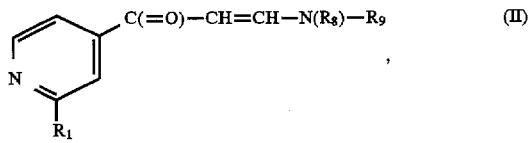

wherein $R_8$ and $R_9$ are each independently of the other lower alkyl and $R_1$ is as defined above, functional groups present in a compound of formula II, with the exception of the groups participating in the reaction, being, if necessary, in protected form, or a salt of such a compound is reacted with a compound of formula III

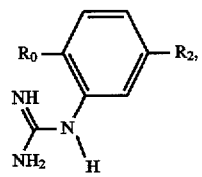

wherein $R_0$ and $R_2$ are as defined above, functional groups present in a compound of formula III, with the exception of the guanidino group participating in the reaction, being, if necessary, in protected form, or with a salt of such a compound, and any protecting groups present are removed, or b) for the preparation of a compound of formula I wherein $R_1$ has the above-mentioned meaning c), d) or g) and $R_0$ and $R_2$ each have any one of the above-mentioned meanings, a compound of formula IV

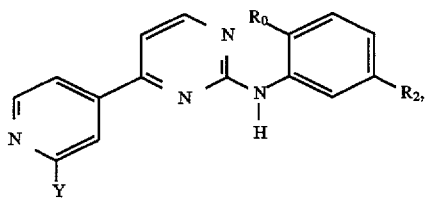

wherein Y is a leaving group and $R_0$ and $R_2$ are as defined above, functional groups present in a compound of formula IV, with the exception of the leaving group participating in the reaction, being, if necessary, in protected form, or a salt of such a compound is reacted with an amine of the formula $$H_2N\text{—}R_{12} \qquad \text{(V)}$$

wherein $R_{12}$ is amino or unsubstituted or amino-substituted cyclohexyl, or is lower alkyl that is substituted by morpholinyl, hydroxy-lower alkylamino, cyano, imidazolyl, guanidyl, amino, lower alkanoylamino, lower alkylamino-carbonylamino, amidino, di-lower alkylamino-cyclohexyl, carboxy, lower alkoxycarbonyl, carbamoyl, N-hydroxycarbamoyl, hydroxy, lower alkoxy, dihydroxyphosphoryloxy, piperazinyl, lower alkanoyl-piperazinyl, formylpiperazinyl, prolylamido or by a radical of the formula $H_2N\text{—}CH(R)\text{—}C(=O)\text{—}NH\text{—}$ wherein R is hydrogen, $C_1\text{-}C_4$alkyl, benzyl, hydroxymethyl, 1-hydroxy-ethyl, mercaptomethyl, 2-methylthio-ethyl, indol-3-yl-methyl, phenyl-methyl, 4-hydroxy-phenyl-methyl, carbamoyl-methyl, 2-carbamoyl-ethyl, carboxy-methyl, 2-carboxy-ethyl, 4-amino-butyl, 3-guanidyl-propyl or R is 1H-imidazol-4-yl-methyl, functional groups present in $R_{12}$ being, if necessary, in protected form, and any protecting groups present are removed, or c) for the preparation of a compound of formula I wherein $R_1$ is N-(amino-lower alkyl)-carbamoyl or N-(hydroxy-lower alkyl)-carbamoyl and $R_0$ and $R_2$ each have any one of the above-mentioned meanings, a carboxylic acid of formula IX

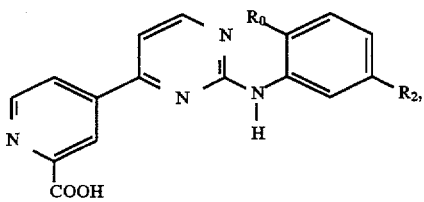

wherein $R_0$ and $R_2$ each have any one of the above-mentioned meanings, functional groups present in $R_2$ being, if necessary, in protected form, or a reactive acid derivative thereof is reacted with an amine of formula X $$H_2N\text{—}R_{13} \qquad \text{(X)},$$

wherein $R_{13}$ is amino-lower alkyl or hydroxy-lower alkyl, the amino or hydroxy group being, if necessary, in protected form, and any protecting groups present are removed, or d) for the preparation of a compound of formula I wherein $R_1$ is morpholinyl, or is piperazinyl that is unsubstituted or substituted by amino-lower alkyl and $R_0$ and $R_2$ each have any one of the above-mentioned meanings, a compound of formula IV

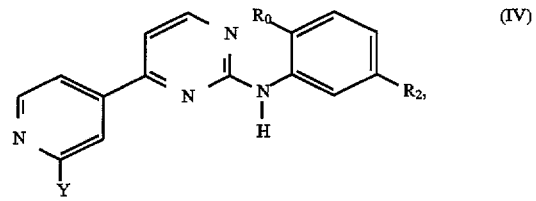

wherein Y is a leaving group and $R_0$ and $R_2$ are as defined above, functional groups present in a compound of formula IV, with the exception of the leaving group participating in the reaction, being, if necessary, in protected form, or a salt of such a compound is reacted with morpholine, or with piperazine that is unsubstituted or substituted by amino-lower alkyl, and any protecting groups present are removed, or e) for the preparation of a compound of formula I wherein $R_2$ is $\text{—}CO_2R_3$, $\text{—}C(=O)\text{—}NH\text{—}(CH_2)_n\text{—}R_4^a$ or $\text{—}C(=O)\text{—}NH\text{—}(CH_2)_n\text{—}N(R_3)\text{—}R_4$, wherein the symbols and substituents are each as defined above, a carboxylic acid of formula XI

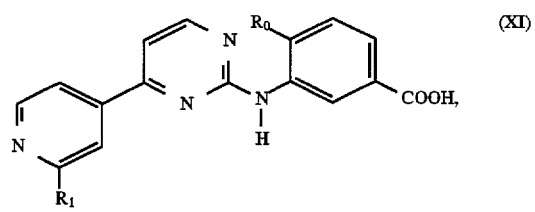

wherein $R_0$ and $R_1$ are as defined above, functional groups present therein being, if necessary, in protected form, or a reactive carboxylic acid derivative thereof is esterified or amidated in an appropriate manner and any protecting groups present are removed, and, if desired, a compound of formula I obtained in accordance with any one of Processes a–e is convened into its salt, or an obtained salt of a compound of formula I is convened into the free compound.

The manner in which the above-mentioned process variants are carried out is explained in detail hereinafter:

General:

The end products of formula I may comprise substituents that can also be used as protecting groups in starting materials for the preparation of other end products of formula I. Within the scope of this text, therefore, unless the context indicates otherwise, only a readily removable group that is not a constituent of the particular end product of formula I desired is referred to as a "protecting group".

Protecting groups and the manner in which they are introduced and removed are described, for example, in "Protective Groups in Organic Chemistry", Plenum Press, London, New York 1973, and in "Methoden der organischen Chemie", Houben-Weyl, 4th edition, Vol. 15/1, Georg-Thieme-Verlag, Stuttgart 1974 and in Theodora W. Greene, "Protective Groups in Organic Synthesis", John Wiley & Sons, New York 1981. A characteristic of protecting groups is that they can be readily removed, that is to say, without undesired secondary reactions taking place, for example by solvolysis, reduction, photolysis or also under physiological conditions.

Hydroxy-protecting groups are, for example, acyl radicals, such as unsubstituted or substituted, for example halogen-substituted, lower alkanoyl, such as 2,2- dichloroacetyl, or acyl radicals of carbonic acid semiesters, especially tert-butoxycarbonyl, unsubstituted or substituted benzyloxycarbonyl, for example 4-nitrobenzyloxycarbonyl, or diphenylethoxycarbonyl, or 2-halo-lower alkoxycarbonyl, such as 2,2,2-trichloroethoxycarbonyl, and also trityl or formyl, or organic silyl or stannyl radicals, and also readily removable etherifying groups, such as tert-lower alkyl, for example tert-butyl, 2-oxa- or 2-thia-aliphatic or -cycloaliphatic hydrocarbon radicals, especially 1-lower alkoxy-lower alkyl or 1-lower alkylthio-lower alkyl, for example methoxymethyl, 1-methoxy-ethyl, 1-ethoxyethyl, methylthiomethyl, 1-methylthioethyl or 1-ethylthioethyl, or 2-oxa- or 2-11thia-cycloalkyl having 5 or 6 ring atoms, for example tetrahydrofuryl or 2-tetrahydropyranyl or corresponding thia analogues, and also unsubstituted or substituted 1-phenyl-lower alkyl, such as unsubstituted or substituted benzyl or diphenylmethyl, suitable substituents of the phenyl radicals being, for example, halogen, such as chlorine, lower alkoxy, such as methoxy, and/or nitro.

A protected amino group may, for example, be in the form of a readily cleavable acyl-amino, arylmethylamino, etherified mercaptoamino, 2-acyl-lower alk-1-en-yl-amino, silylamino or stannylamino group or in the form of an azido group.

In a corresponding acylamino group, acyl is, for example, the acyl radical of an organic carboxylic acid having, for example, up to 18 carbon atoms, especially of an alkanecarboxylic acid that is unsubstituted or substituted, for example, by halogen or by aryl, or of a benzoic acid that is unsubstituted or substituted, for example, by halogen, lower alkoxy or by nitro, or of a carbonic acid semiester. Such acyl groups are, for example, lower alkanoyl, such as formyl, acetyl or propionyl, halo-lower alkanoyl, such as 2-haloacetyl, especially 2-chloro-, 2-bromo-, 2-iodo-, 2,2,2-trifluoro- or 2,2,2-trichloro-acetyl, benzoyl that is unsubstituted or substituted, for example, by halogen, lower alkoxy or by nitro, for example benzoyl, 4-chlorobenzoyl, 4-methoxybenzoyl or 4-nitrobenzoyl, or lower alkoxycarbonyl that is branched in the 1-position of the lower alkyl radical or suitably substituted in the 1- or 2-position, especially tert-lower alkoxycarbonyl, for example tert-butoxycarbonyl, arylmethoxycarbonyl having one or two aryl radicals that are preferably phenyl that is unsubstituted or mono- or poly-substituted, for example, by lower alkyl, especially tert-lower alkyl, such as tert-butyl, lower alkoxy, such as methoxy, hydroxy, halogen, for example chlorine, and/or by nitro, such as unsubstituted or substituted benzyloxycarbonyl, for example 4-nitrobenzyloxycarbonyl, or substituted diphenylmethoxycarbonyl, for example benzhydryloxycarbonyl or di(4-methoxyphenyl)methoxycarbonyl, aroylmethoxycarbonyl wherein the aroyl group is preferably benzoyl that is unsubstituted or substituted, for example, by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, or 2-(trisubstituted silyl)-ethoxycarbonyl wherein the substituents are each independently of the others an aliphatic, araliphatic, cycloaliphatic or aromatic hydrocarbon radical that is unsubstituted or substituted, for example, by lower alkyl, lower alkoxy, aryl, halogen or by nitro, and contains up to 15 carbon atoms, such as corresponding unsubstituted or substituted lower alkyl, phenyl-lower alkyl, cycloalkyl or phenyl, for example 2-tri-lower alkylsilylethoxycarbonyl, such as 2-trimethylsilylethoxycarbonyl or 2-(di-n-butylmethyl-silyl)-ethoxycarbonyl, or 2-triarylsilylethoxycarbonyl, such as 2-triphenylsilylethoxycarbonyl.

Other acyl radicals suitable as amino-protecting groups are also corresponding radicals of organic phosphoric, phosphonic or phosphinic acids, such as di-lower alkylphosphoryl, for example dimethylphosphoryl, diethylphosphoryl, di-n-propylphosphoryl or diisopropylphosphoryl, dicycloalkylphosphoryl, for example dicyclohexylphosphoryl, unsubstituted or substituted diphenylphosphoryl, for example diphenylphosphoryl, unsubstituted or substituted, for example nitro-substituted, di(phenyl-lower alkyl)phosphoryl, for example dibenzylphosphoryl or di(4-nitrobenzyl)phosphoryl, unsubstituted or substituted phenyloxyphenylphosphonyl, for example phenyloxyphenylphosphonyl, di-lower alkylphosphinyl, for example diethylphosphinyl, or unsubstituted or substituted diphenylphosphinyl, for example diphenylphosphinyl.

In an arylmethylamino group that is a mono-, di- or, especially, tri-arylmethylamino group, the aryl radicals are especially unsubstituted or substituted phenyl radicals. Such groups are, for example, benzyl-, diphenylmethyl- and, especially, trityl-amino.

An etherified mercapto group in an amino group protected by such a radical is especially arylthio or aryl-lower alkylthio wherein aryl is especially phenyl that is unsubstituted or substituted, for example, by lower alkyl, such as methyl or tert-butyl, lower alkoxy, such as methoxy, halogen, such as chlorine, and/or by nitro. A corresponding amino-protecting group is, for example, 4-nitrophenylthio.

In a 2-acyl-lower alk-1-en-1-yl radical that can be used as an amino-protecting group, acyl is, for example, the corresponding radical of a lower alkanecarboxylic acid, of a benzoic acid that is unsubstituted or substituted, for example, by lower alkyl, such as methyl or tert-butyl, lower alkoxy, such as methoxy, halogen, such as chlorine, and/or by nitro, or especially of a carbonic acid semiester, such as a carbonic acid lower alkyl semiester. Corresponding protecting groups are especially 1-lower alkanoyl-prop-1-en-2-yl, for example 1-acetyl-prop-1-en-2-yl, or 1-lower alkoxycarbonyl-prop-1-en-2-yl, for example 1-ethoxycarbonyl-prop-1-en-2-yl.

Preferred amino-protecting groups are acyl radicals of carbonic acid semiesters, especially tert-butoxycarbonyl, benzyloxycarbonyl that is unsubstituted or substituted, for example, as indicated, for example 4-nitrobenzyloxycarbonyl, or diphenylmethoxycarbonyl, or 2-halo-lower alkoxycarbonyl, such as 2,2,2-trichloroethoxycarbonyl, and also trityl or formyl. The removal of the protecting groups that are not constituents of the desired end product of formula I is effected in a manner known per se, for example by solvolysis, especially hydrolysis, alcoholysis or acidolysis, or by means of reduction, especially hydrogenolysis or chemical reduction, as appropriate stepwise or simultaneously.

A protected amino group is freed in a manner known per se and, depending on the nature of the protecting groups, in various manners, preferably by solvolysis or reduction. 2-halo-lower alkoxycarbonylamino (where appropriate after conversion of a 2-bromo-lower alkoxycarbonylamino group into a 2-iodo-lower alkoxycarbonylamino group), aroylmethoxycarbonylamino or 4-nitrobenzyloxycarbonylamino can be cleaved, for example, by treatment with a suitable chemical reducing agent, such as zinc in the presence of a suitable carboxylic acid, such as aqueous acetic acid. Aroylmethoxycarbonylamino can also be cleaved by treatment with a nucleophilic, preferably saltforming reagent, such as sodium thiophenolate, and 4-nitro-benzyloxycarbonylamino also by treatment with an alkali metal dithionite, for example sodium dithionite. Unsubstituted or substituted diphenylmethoxycarbonylamino, tert-lower alkoxycarbonylamino or 2-tri-substituted silylethoxycarbonylamino can be cleaved by treatment with a suitable acid, for example formic acid or trifluoroacetic acid, unsubstituted or substituted benzyloxycarbonylamino, for example, by hydrogenolysis, that is to say by treatment with hydrogen in the presence of a suitable hydrogenation catalyst, such as a palladium catalyst, unsubstituted or substituted triarylmethylamino or formylamino, for example, by treatment with an acid, such as a mineral acid, for example hydrochloric acid, or an organic acid, for example formic, acetic or trifluoroacetic acid, where appropriate in the presence of water, and an amino group protected by an organic silyl group can be freed, for example, by hydrolysis or alcoholysis. An amino group protected by 2-haloacetyl, for example 2-chloroacetyl, can be freed by treatment with thiourea in the presence of a base, or with a thiolate salt, such as an alkali metal thiolate, of the thiourea, and subsequent solvolysis, such as alcoholysis or hydrolysis, of the resulting condensation product. An amino group protected by 2-substituted silylethoxycarbonyl can also be convened into the free amino group by treatment with a hydrofluoric acid salt yielding fluoride anions.

A hydroxy group protected by a suitable acyl group, an organic silyl group or by unsubstituted or substituted 1-phenyl-lower alkyl is freed analogously to a correspondingly protected amino group. Hydroxy protected by unsubstituted or substituted 1-phenyl-lower alkyl, for example benzyl, is freed preferably by catalytic hydrogenation, for example in the presence of a palladium-on-carbon catalyst. A hydroxy group protected by 2,2-dichloroacetyl is freed, for example, by basic hydrolysis, and a hydroxy group etherified by tert-lower alkyl or by a 2-oxa- or 2-thia-aliphatic or -cycloaliphatic hydrocarbon radical is freed by acidolysis, for example by treatment with a mineral acid or a strong carboxylic acid, for example trifluoroacetic acid. Hydroxy etherified by an organic silyl radical, for example trimethylsilyl, can also be freed by a hydrofluoric acid salt yielding fluoride anions, for example tetrabutylammonium fluoride.

Process a:

Preferably, $R_8$ and $R_9$ are each methyl.

Free functional groups in a compound of formula II, which are advantageously protected by readily removable protecting groups, are especially amino groups in the radical $R_1$ and the imino group of 1H-indolyl. The imino group can be protected, for example, by benzyl.

Free functional groups in a compound of formula III, which are advantageously protected by readily removable protecting groups, are especially amino groups, but also hydroxy and carboxy groups.

A salt of a compound of formula II or III is preferably an acid addition salt, for example a nitrate or one of the acid addition salts mentioned for the end products of formula I.

The reaction is carried out in a suitable solvent or dispersing agent, for example a suitable alcohol, such as 2-methoxy-ethanol or a suitable lower alkanol, for example isopropanol or isobutanol, at a temperature of from room temperature (approximately 20° C.) to 150° C., for example under reflux. Especially when a compound of formula II or especially III is used as salt, that salt is converted into the free compound, preferably in situ, by the addition of a suitable base, such as an alkali metal hydroxide, for example sodium hydroxide.

The starting material of formula II is obtained by reacting a compound of formula VI

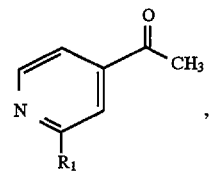

(VI)

wherein $R_1$ is as defined above, functional groups present therein being, if necessary, in protected form, or a salt of such a compound with a compound of formula VII

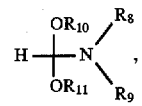

(VII)

wherein $R_{10}$ and $R_{11}$ are each lower alkyl and the other substituents are as defined above, analogously to the procedure described in the European Patent Application having the publication number 233 461. Typical representatives of a compound of formula VII are N,N-dimethylformamide dimethylacetal and N,N-dimethylformamide diethylacetal. The reaction is effected while heating the reactants of formulae VI and VII, for example for 1–24 hours, in the absence or, if necessary, in the presence of a solvent, at a temperature of approximately from 50° C. to 150° C., for example at approximately 110° C.

Alternatively, the starting material of formula II can also be obtained by reacting a compound of formula VI with formic acid ethyl ester of the formula H—C(=O)—O—CH$_2$—CH$_3$ and reacting the resulting product with an amine of the formula H—N($R_8$)—$R_9$ wherein the substituents are as defined above.

The starting material of formula III is obtained in the form of an acid addition salt by reacting an aniline derivative of formula VIII

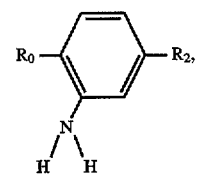

(VIII)

wherein $R_0$ and $R_2$ are as defined above, with cyanamide (NC—N$_2$). The reaction is effected in a suitable solvent or dispersing agent, for example a suitable alcohol, for example a suitable lower alkanol, such as ethanol, for example α) in the presence of equimolar amounts of the salt-forming acid, for example nitric acid, or β) in the presence of a clear, for example 60%, excess of a mineral acid, such as hydrochloric acid, an ammonium salt of the desired salt-forming acid, for example ammonium nitrate, being added when the reaction is complete, at a temperature of from room temperature to 150° C., for example under reflux.

Process b:

A leaving group Y in a compound of formula IV is reactive esterified hydroxy, for example hydroxy esterified by a strong inorganic or organic acid, such as by a mineral acid, for example a hydrohalic acid, such as hydrochloric, hydrobromic or hydriodic acid, also sulfuric acid or a sulfuryl halide, for example sulfuryl fluoride, or by a strong organic sulfonic acid, such as a lower alkanesulfonic acid that is unsubstituted or substituted, for example, by halogen, such as fluorine, or an aromatic sulfonic acid, for example a benzenesulfonic acid that is unsubstituted or substituted by lower alkyl, such as methyl, halogen, such as bromine, and/or by nitro, for example a methanesulfonic, trifluoromethanesulfonic or p-toluenesulfonic acid. Y is preferably halogen, such as, especially, chlorine.

The reaction is preferably carded out in the presence of an excess of the amine of formula V, which can, where appropriate, also be used as solvent, and, if necessary, in the presence of an inert solvent, such as dimethyl sulfoxide, at a temperature of from room temperature to +150° C., for example at 100° C.

The starting material of formula IV can be prepared, for example, analogously to Process a. For example, first 4-acetyl-pyridine can be oxidised with m-chloro-perbenzoic acid in a suitable solvent, such as methylene chloride, for example under reflux, to 4-acetylpyridine N-oxide. 4-acetyl-pyridine N-oxide is then convened with phosphorus oxychloride in a suitable inert solvent, such as toluene, for example at approximately 100° C., into 4-acetyl-2-chloro-pyridine. The 4-acetyl-2-chloro-pyridine obtained is then reacted with a compound of formula VII shown in Process a to give a compound analogous to formula II shown above under Process a wherein $R_1$ is chlorine. The compound so obtained is then reacted analogously to Process a with a compound of formula III to form the starting material of formula IV.

Alternatively, the starting material of formula IV can be obtained by converting 4-acetylpyridine N-oxide with dimethylformamide diethylacetal of formula VII, which, for example, simultaneously serves as solvent, for example at approximately 110° C., into 3-dimethylamino-1-(N-oxido-pyridyl)-2-propen-1-one, such as 3-dimethylamino-1-(N-oxido-4-pyridyl)-2-propen-1-one, which is then reacted with an $R_2$-phenyl-guanidine of formula III wherein $R_2$ is as defined above, or preferably with a suitable salt, for example a nitram, thereof in a suitable solvent, such as isopropanol, and in the presence of a suitable base, such as sodium hydroxide, for example under reflux, to form an N-oxidopyridyl compound analogous to formula IV wherein Y is oxido. The N-oxido-pyridyl compound so obtained is then converted with phosphorus oxychloride into a compound of formula IV wherein Y is chlorine. The reaction with phosphorus oxychloride can be carried out, for example, in the absence of a solvent at approximately 100° C. Alternatively, it is possible to use phosphorus oxychloride together with a suitable amine, such as diisopropylamine in a suitable solvent, for example a chlorinated hydrocarbon, such as chloroform, at approximately room temperature. Another possibility is to use phosphorus oxychloride in a suitable solvent, such as chloroform, toluene or xylene, at elevated temperature, for example under reflux.

Process c:

Free functional groups in the radical $R_2$ of a compound of formula IX, which are advantageously protected by readily removable protecting groups, are especially carboxy groups, but also amino groups.

A reactive derivative of a compound of formula IX is especially a reactive (activated) ester, a reactive anhydride or a reactive cyclic amide.

Reactive (activated) esters of an acid of formula IX are especially esters unsaturated at the linking carbon atom of the esterifying radical, for example of the vinyl ester type, such as vinyl esters themselves (which can be obtained, for example, by transesterifying a corresponding ester with vinyl acetate; activated vinyl ester method), carbamoyl vinyl esters (which can be obtained, for example, by treating the corresponding acid with an isoxazolium reagent; 1,2-oxazolium or Woodward method), or 1-lower alkoxyvinyl esters (which can be obtained, for example, by treating the corresponding acid with a lower alkoxyacetylene; ethoxyacetylene method), or esters of the amidino type, such as N,N'-di-substituted amidino esters (which can be obtained, for example, by treating the corresponding acid with a suitable N,N'-di-substituted carbodiimide, for example N,N'-dicyclohexylcarbodiimide; carbodiimide method), or N,N-di-substituted amidino esters (which can be obtained, for example, by treating the corresponding acid with an N,N-di-substituted cyanamide; cyanamide method), suitable aryl esters, especially phenyl esters suitably substituted by electron-attracting substituents (which can be obtained, for example, by treating the corresponding acid with a suitably substituted phenol, for example 4-nitrophenol, 4-methylsulfonyl-phenol, 2,4,5-trichlorophenol, 2,3,4,5,6-pentachlorophenol or 4-phenyldiazophenol, in the presence of a condensation agent, such as N,N'-dicyclohexylcarbodiimide; activated aryl esters method), cyanomethyl esters (which can be obtained, for example, by treating the corresponding acid with chloroacetonitrile in the presence of a base; cyanomethyl esters method), thio esters, especially unsubstituted or substituted, for example nitro-substituted, phenylthio esters (which can be obtained, for example, by treating the corresponding acid with unsubstituted or substituted, for example nitro-substituted, thiophenols, inter alia by the anhydride or carbodiimide method; activated thiol esters method), amino or amido esters (which can be obtained, for example, by treating the corresponding acid with an N-hydroxy-amino or N-hydroxy-amido compound, for example N-hydroxy-succinimide, N-hydroxy-piperidine, N-hydroxyphthalimide or 1-hydroxy-benzotriazole, for example by the anhydride or carbodiimide method; activated N-hydroxy esters method) or silyl esters (which can be obtained, for example, by treating the corresponding acid with a silylating agent, for example hexamethyldisilazane, and which react readily with hydroxy groups but not with amino groups).

Anhydrides of an acid of formula IX may be symmetric or preferably mixed anhydrides of those acids, for example anhydrides with inorganic acids, such as acid halides, especially acid chlorides (which can be obtained, for example, by treating the corresponding acid with thionyl chloride, phosphorus pentachloride or oxalyl chloride; acid chloride method), azides (which can be obtained, for example, from a corresponding acid ester by way of the corresponding hydrazide and treatment thereof with nitrous acid; azide method), anhydrides with carbonic acid semi-derivatives, such as with corresponding esters, for example carbonic acid lower alkyl semiesters (which can be obtained, for example, by treating the corresponding acid with haloformic acid lower alkyl esters, such as chloroformic acid lower alkyl esters, or with a 1-lower alkoxycarbonyl-2-lower alkoxy-1, 2-dihydroquinoline, for example 1-lower alkoxycarbonyl-2-ethoxy-1,2-dihydroquinoline; mixed O-alkylcarbonic acid anhydrides method), or anhydrides with dihalogenated, especially dichlorinated, phosphoric acid (which can be obtained, for example, by treating the corresponding acid with phosphorus oxychloride; phosphorus oxychloride method), or anhydrides with organic acids, such as mixed anhydrides with organic carboxylic acids (which can be obtained, for example, by treating the corresponding acid with an unsubstituted or substituted lower alkane- or phenylalkane-carboxylic acid halide, for example phenylacetic acid chloride, pivalic acid chloride or trifluoroacetic acid chloride; mixed carboxylic acid anhydrides method) or with organic sulfonic acids (which can be obtained, for example, by treating a salt, such as an alkali metal salt, of the corresponding acid with a suitable organic sulfonic acid halide, such as a lower alkane- or aryl-sulfonic acid chloride, for example methane- or p-toluene-sulfonic acid chloride; mixed sulfonic acid anhydrides method) and symmetric anhydrides (which can be obtained, for example, by condensing the corresponding acid in the presence of a carbodiimide or 1-diethylaminopropyne; symmetric anhydrides method).

Suitable cyclic amides are especially amides having five-membered diazacycles of aromatic character, such as amides with imidazoles, for example imidazole (which can be obtained, for example, by treating the corresponding acid with N,N'-carbonyldiimidazole; imidazolide method), or pyrazoles, for example 3,5-dimethylpyrazole (which can be obtained, for example, by way of the acid hydrazide by treatment with acetylacetone; pyrazolide method).

Derivatives of acids of formula IX that are used as acylating agents can also be formed in situ. For example, N,N'-di-substituted amidino esters can be formed in situ by reacting a mixture of the starting material of formula X and the acid used as acylating agent in the presence of a suitable N,N-di-substituted carbodiimide, for example N,N'-dicyclohexylcarbodiimide. In addition, amino or amido esters of the acids used as acylating agents can be formed in the presence of the starting material of formula X to be acylated, by reacting a mixture of the corresponding acid and amino starting materials in the presence of an N,N'-di-substituted carbodiimide, for example N,N'-dicyclohexylcarbodiimide, and of an N-hydroxy-amine or N-hydroxy-amide, for example N-hydroxysuccinimide, where appropriate in the presence of a suitable base, for example 4-dimethylaminopyridine.

The reaction is preferably carried out by reacting a reactive carboxylic acid derivative of a compound of formula IX with a compound of formula X, the amino group participating in the reaction being in protected form. In a preferred form of the reaction, a solution of the starting material of formula IX in dimethylformamide is stirred together with N-ethyl-N'-(3-dimethylaminopropyl)-carbodiimide hydrochloride and N-hydroxysuccinimide for a few hours at room temperature, and the reaction mixture so obtained is then added dropwise to a solution of the amine of formula X in dimethylformamide.

The reaction can be carried out in a manner known per se, the reaction conditions depending especially upon whether and how the carboxy group of the acylating agent has been activated, generally in the presence of a suitable solvent or diluent or a mixture thereof, and, if necessary, in the presence of a condensation agent which, for example when the carboxy group participating in the reaction is in the form of an anhydride, may also be an acid-binding agent, with cooling or heating, for example in a temperature range of from approximately −30° C. to approximately +150° C., especially approximately from 0° C. to +100° C., preferably from room temperature (approximately +20° C.) to +70° C., in an open or closed reaction vessel and/or in the atmosphere of an inert gas, for example nitrogen. Customary condensation agents are, for example, carbodiimides, for example N,N'-diethyl-, N,N'-dipropyl-, N,N'-dicyclohexyl- or N-ethyl-N'-(3-dimethylaminopropyl)-carbodiimide, suitable carbonyl compounds, for example carbonyldiimidazole, or 1,2-oxazolium compounds, for example 2-ethyl-5-phenyl-1,2-oxazolium-3'-sulfonate and 2-tert-butyl-5-methyl-isoxazolium perchlorate, or a suitable acylamino compound, for example 2-ethoxy-1-ethoxycarbonyl-1,2-dihydroquinoline. Customary acid-binding condensation agents are, for example, alkali metal carbonates or hydrogen carbonates, for example sodium or potassium carbonate or hydrogen carbonate (customarily together with a sulfate), or organic bases, such as customarily pyridine or sterically hindered tri-lower alkylamines, for example N,N-diisopropyl-N-ethylamine.

The starting material of formula IX is obtained, for example, by hydrolysis of the corresponding 3-cyano-pyridyl compound. The hydrolysis of cyano to carboxy is carried out in a suitable solvent, such as an alcohol, such as ethanol, for example in the presence of a suitable base, such as aqueous sodium hydroxide solution, at temperatures of from room temperature to +150° C., for example at 60° C. The 3-cyano-pyridyl compound is obtained from the corresponding N-oxido-pyridyl compound. For that purpose, the N-oxido group is first converted into a leaving group, for example by reaction with a suitable reactive carboxylic acid derivative or sulfonic acid derivative, for example with a suitable lower alkanoic acid chloride, lower alkanoic acid anhydride, such as acetic anhydride, N,N-di-methyl-carbamoyl chloride, toluenesulfonyl chloride, methanesulfonyl chloride or tri-fluoromethanesulfonyl chloride. The cyano group is then introduced with a suitable nucleophile which acts in the ortho-position with respect to the pyridine nitrogen. A nucleophile that introduces cyano is, for example, a suitable silyl cyanide, such as tri-lower alkyl-silyl cyanide, for example trimethylsilyl cyanide. The introduction of cyano is carried out in a suitable solvent, such as acetonitrile, at temperatures of approximately from 0° C. to 150° C., preferably approximately from room temperature to 100° C.

The N-oxido-pyridyl compound is obtained by oxidising a corresponding pyridyl compound with a suitable oxidising agent, such as a suitable peracid, for example a suitable perbenzoic acid, such as especially m-chloro-perbenzoic acid, in an inert solvent, such as methylene chloride, at room temperature.

Process d:

Process d is carried out analogously to Process b.

Process e:

Process e is carried out analogously to Process c. For example, a compound of formula XI can be esterified in the presence of a strong acid, such as concentrated sulfuric acid, the latter acting simultaneously as an agent binding the elements of water, with the desired alcohol $R_3$—OH, which may serve simultaneously as solvent. Alternatively, a reactive carboxylic acid derivative of a compound of formula XI, for example a suitable ester, such as a methyl ester, can be amidated with an amine of the formula $H_2N$—$(CH_2)_n$—$R_4^a$ or $H_2N$—$(CH_2)_n$—$N(R_3)$—$R_4$.

Acid addition salts of compounds of formula I are obtained in customary manner, for example by treatment with an acid or a suitable anion exchange reagent.

Acid addition salts can be converted in customary manner into the free compounds, for example by treatment with a suitable basic agent.

Mixtures of isomers can be separated into the individual isomers in a manner known per se, for example by fractional crystallisation, chromatography, etc.

The processes described above, including the processes for removing protecting groups and the additional process measures are, unless otherwise indicated, carried out in a manner known per se, for example in the presence or absence of preferably inert solvents or diluents, if necessary in the presence of condensation agents or catalysts, at reduced or elevated temperature, for example in a temperature range of from approximately −20° C. to approximately 150° C., especially from approximately 0° C. to approximately +70° C., preferably from approximately +10° C. to approximately +50° C., principally at room temperature, in a suitable vessel and, if necessary, in an inert gas atmosphere, for example a nitrogen atmosphere.

Taking into account all the substituents in the molecule, if necessary, for example if readily hydrolysable radicals are present, especially mild reaction conditions are to be used, such as short reaction times, the use of mild acidic or basic agents in low concentration, stoichiometric ratios, and the selection of suitable catalysts, solvents, temperature conditions and/or pressure conditions.

The invention relates also to those forms of the process in which a compound obtainable as intermediate at any stage of the process is used as starting material and the remaining process steps are carried out or the process is discontinued at any stage or a starting material is formed under the reaction conditions or is used in the form of a reactive derivative or salt. The starting materials used are preferably those which, according to the process, result in the compounds described above as being especially valuable.

The invention relates preferably to processes for the preparation of a compound of formula Ia

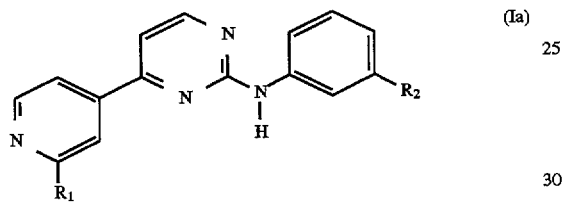

(Ia)

wherein
R$_1$ is
a) N-(amino-lower alkyl)-carbamoyl,
b) N-(hydroxy-lower alkyl)-carbamoyl,
c) hydrazino,
d) cyclohexyl-amino that is unsubstituted or substituted by amino, or
e) lower alkylamino that is substituted by cyano, imidazolyl, guanidyl, amino, lower alkanoylamino, lower alkylamino-carbonylamino, amidino, di-lower alkylamino-cyclohexyl, carboxy, lower alkoxycarbonyl, carbamoyl, N-hydroxy-carbamoyl, hydroxy, lower alkoxy, dihydroxyphosphoryloxy, piperazinyl, lower alkanoyl-piperazinyl, formylpiperazinyl, prolylamido or by a radical of the formula H$_2$N—CH(R)—C(=O)—NH— wherein R is hydrogen, C$_1$–C$_4$alkyl, benzyl, hydroxymethyl, 1-hydroxy-ethyl, mercaptomethyl, 2-methylthio-ethyl, indol-3-yl-methyl, phenyl-methyl, 4-hydroxy-phenyl-methyl, carbamoyl-methyl, 2-carbamoyl-ethyl, carboxy-methyl, 2-carboxy-ethyl, 4-amino-butyl, 3-guanidyl-propyl or R is 1H-imidazol-4-yl-methyl, and R$_2$ is C$_1$–C$_6$alkyl, C$_1$–C$_3$alkoxy, chlorine, bromine, iodine, trifluoromethyl, hydroxy, phenyl, amino, mono (C$_1$–C$_3$alkyl)amino, di(C$_1$–C$_3$alkyl)amino, C$_2$–C$_4$alkanoyl, propenyloxy, carboxy, carboxymethoxy, ethoxycarbonyl-methoxy, sulfanilamido, N,N-di(C$_1$–C$_3$alkyl)sulfanilamido, N-methyl-piperazinyl, piperidinyl, 1H-imidazol-1-yl, 1H-triazol-1-yl, 1H-benzimidazol-2-yl, 1-naphthyl, cyclopentyl, 3,4-dimethyl-benzyl or a radical of one of the formulae:
—CO$_2$R$_3$, —NH—C(=O)—R$_3$, —N(R$_3$)—C(=O)—R$_4$, —O—(CH$_2$)$_n$—N(R$_3$)—R$_4$, —C(=O)—NH—(CH$_2$)$_n$—N(R$_3$)—R$_4$, —CH(CH$_3$)—NH—CHO, —C(CH$_3$)=N—OH, —C(CH$_3$)=N—O—CH$_3$,
—CH(CH$_3$)—NH$_2$, —NH—CH$_2$—C(=O)—N(R$_3$)—R$_4$,

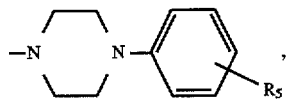

—(CH$_2$)$_m$—R$_6$, —X—(CH$_2$)$_m$—R$_6$ and

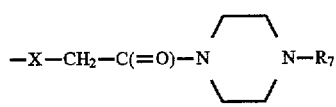

wherein R$_3$ arid R$_4$ are each independently of the other C$_1$–C$_3$alkyl, X is oxygen or sulfur, m is 1, 2 or 3, n is 2 or 3, R$_5$ is hydrogen, C$_1$–C$_3$alkyl, C$_1$–C$_3$alkoxy, chlorine, bromin iodine or trifluoromethyl, R$_6$ is 1H-imidazol-1-yl or morpholinyl, and R$_7$ is C$_1$–C$_3$alkyl or is phenyl that is unsubstituted or mono-substituted by C$_1$–C$_3$alkyl, halogen or by trifluoromethyl, or a salt thereof, wherein
a) a compound of formula II

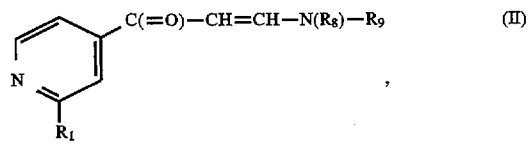

(II)

wherein R$_8$ and R$_9$ am each independently of the other lower alkyl and R$_1$ is as defined above, functional groups present in a compound of formula II, with the exception of the groups participating in the reaction, being, if necessary, in protected form, or a salt of such a compound is reacted with a compound of formula IIIa

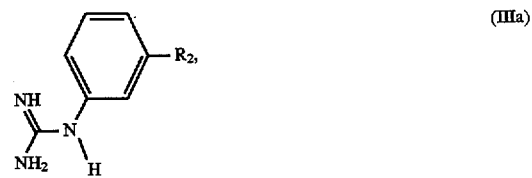

(IIIa)

wherein R$_2$ is as defined above, functional groups present in a compound of formula IIIa, with the exception of the guanidino group participating in the reaction, being, if necessary, in protected form, or with a salt of such a compound, and any protecting groups present are removed, or
b) for the preparation of a compound of formula Ia wherein R$_1$ has any one of the above-mentioned meanings c) to e) and R$_2$ has any one of the above-mentioned meanings, a compound of formula IVa

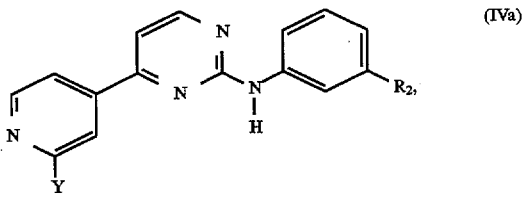

(IVa)

wherein Y is a leaving group and R$_2$ is as defined above, functional groups present in a compound of formula IVa, with the exception of the leaving group participating in the reaction, being, if necessary, in protected form, or a salt of such a compound is reacted with an amine of the formula

   (V)

wherein R$_{12}$ is amino or unsubstituted or amino-substituted cyclohexyl, or is lower alkyl that is substituted by cyano, imidazolyl, guanidyl, amino, lower alkanoylamino, lower alkylamino-carbonylamino, amidino, di-lower alkylamino-cyclohexyl, carboxy, lower alkoxycarbonyl, carbamoyl, N-hydroxy-carbamoyl, hydroxy, lower alkoxy, dihydroxyphosphoryloxy, piperazinyl, lower alkanoyl-piperazinyl, formylpiperazinyl, prolylamido or by a radical of the formula H$_2$N—CH(R)—C(=O)—NH— wherein R is hydrogen, C$_1$-C$_4$alkyl, benzyl, hydroxymethyl, 1-hydroxy-ethyl, mercaptomethyl, 2-methylthio-ethyl, indol-3-yl-methyl, phenyl-methyl, 4-hydroxy-phenyl-methyl, carbamoyl-methyl, 2-carbamoylethyl, carboxy-methyl, 2-carboxy-ethyl, 4-amino-butyl, 3-guanidyl-propyl or R is 1H-imidazol-4-yl-methyl, functional groups present in R$_{12}$ being, if necessary, in protected form, and any protecting groups present are removed, or c) for the preparation of a compound of formula Ia wherein R$_1$ is N-(amino-lower alkyl)-carbamoyl or N-(hydroxy-lower alkyl)-carbamoyl and R$_2$ has any one of the above-mentioned meanings, a carboxylic acid of formula IXa

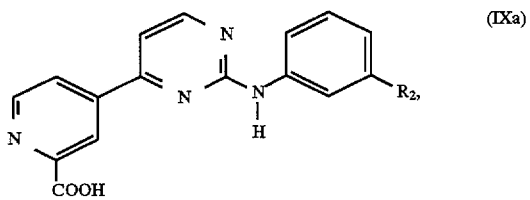   (IXa)

wherein R$_2$ has any one of the above-mentioned meanings, or a reactive acid derivative thereof is reacted with an amine of formula X

   (X), wherein R$_{13}$ is amino-lower alkyl or hydroxy-lower alkyl, the amino or hydroxy group being, if necessary, in protected form, and any protecting groups present are removed, and, if desired, a compound of formula I obtained in accordance with any one of Processes a–c is convened into its salt or an obtained salt of a compound of formula I is convened into the free compound.

The present invention relates also to novel starting materials and/or intermediates and to processes for the preparation thereof. The starting materials used and the reaction conditions chosen are preferably such that the compounds described in this Application as being especially preferred are obtained.

The invention relates also to a method of treating warm-blooded animals suffering from a tumour disease, which method comprises administering to warm-blooded animals requiring such treatment an amount that is effective in inhibiting tumours of a compound of formula I or of a pharmaceutically acceptable salt thereof. The invention relates also to the use of a compound of formula I or of a pharmaceutically acceptable salt thereof in the inhibition of protein kinase C in warm-blooded animals or in the preparation of pharmaceutical compositions for use in the therapeutic treatment of the human or animal body. Depending on the species, age, individual condition, mode of administration and the particular clinical picture, effective doses, for example daily doses of approximately 1–1000 mg, especially 50–500 mg, are administered to a warm-blooded animal of approximately 70 kg body weight.

The invention relates also to pharmaceutical compositions comprising an effective amount, especially an amount effective in the prophylaxis or treatment of one of the above-mentioned disorders, of the active ingredient together with pharmaceutically acceptable carriers that are suitable for topical, enteral, for example oral or rectal, or parenteral administration and that may be inorganic or organic, solid or liquid. There are used for oral administration especially tablets or gelatin capsules that comprise the active ingredient together with diluents, for example lactose, dextrose, sucrose, mannitol, sorbitol, cellulose and/or glycerol, and/or lubricants, for example silica, talc, stearic acid or salts thereof, such as magnesium or calcium stearate, and/or polyethylene glycol. Tablets may also comprise binders, for example magnesium aluminium silicate, starches, such as corn, wheat or rice starch, gelatin, methylcellulose, sodium carboxymethylcellulose and/or polyvinylpyrrolidone, and, if desired, disintegrators, for example starches, agar, alginic acid or a salt thereof, such as sodium alginate, and/or effervescent mixtures, or adsorbents, dyes, flavourings and sweeteners. It is also possible to use the pharmacologically active compounds of the present invention in the form of parenterally administrable compositions or in the form of infusion solutions. Such solutions are preferably isotonic aqueous solutions or suspensions which, for example in the case of lyophilised compositions that comprise the active ingredient alone or together with a carrier, for example mannitol, can be made up prior to use. The pharmaceutical compositions may be sterilised and/or may comprise excipients, for example preservatives, stabilisers, wetting agents and/or emulsifiers, solubilisers, salts for regulating the osmotic pressure and/or buffers. The present pharmaceutical compositions, which may, if desired, comprise other pharmacologically active substances, such as antibiotics, are prepared in a manner known per se, for example by means of conventional mixing, granulating, confectioning, dissolving or lyophilising processes, and comprise approximately from 1% to 100%, especially from approximately 1% to approximately 20%, active ingredient(s).

The following Examples illustrate the invention without limiting it in any way. The R$_f$ values are determined on silica gel thin-layer plates (Merck, Darmstadt, Germany). The ratio of the eluants in the eluant mixtures used is indicated in parts by volume (v/v) and temperatures are indicated in degrees Celsius.

Abbreviations:
conc.: concentrated
HV: high vacuum
RF: reflux
RT: room temperature
h: hour(s)

The abbreviations in respect of NMR spectra have the following meanings:
br: broad
d: doublet
H: hydrogen
m: multiplet
s: singlet

EXAMPLE 1

50 mg (0.143 mmol) of N-(3-trifluoromethyl-phenyl)-4-(2-chloro4-pyridyl)-2-pyrimidineamine are stirred for 44 h at 100° in 1 ml of 3-amino-1-propanol. Concentration by evaporation and chromatography (methylene chloride:methanol=9:1) give N-(3-trifluoromethyl-phenyl)-4-[2-(3-hydroxy-propyl-amino)-4-pyridyl]-2-pyrimidineamine; $R_f$=0.1 (methylene chloride:methanol=95:5), FAB-MS: 390, m.p. 158°–163°.

The starting material is obtained in the following manner:

Stage 1.1: 24.61 g (177.62 mmol) of 2-chloro-4-cyanopyridine are placed in 1.25 litres of diethyl ether under nitrogen, and 120 ml (22% in tetrahydrofuran, 353 mmol) of methyl-magnesium chloride are added. The red suspension is stirred for 40 h at RT, poured onto 1.25 litres of ice/water and 250 ml of 6N HCl and stirred for 14 h at RT. Extraction with diethyl ether and methylene chloride, drying with MgSO$_4$ and concentration give 4-acetyl-2-chloro-pyridine; $R_f$=0.5 (methylene chloride:methanol=9:1).

Alternatively, 4-acetyl-2-chloro-pyridine can be obtained in the following manner:

5.0 g (36.5 mmol) of 4-acetyl-pyridine N-oxide and 6.64 ml (73 mmol) of phosphorus oxychloride are stirred in 50 ml of toluene for 2 h at 100°. The reaction mixture is stirred at 50° into 500 ml of 10N sodium hydroxide solution, extracted with ethyl acetate and treated with Tonsil (Fluka; bentonite—colloidal aqueous aluminium silicate). Concentration and crystallisation (diethyl ether/n-hexane) give 4-acetyl-2-chloro-pyridine;

m.p. 35°, FAB-MS: 156 (M$^+$+H).

The 4-acetyl-pyridine N-oxide used is prepared in the following manner: 11.0 ml (100 mmol) of 4-acetyl-pyridine and 31.3 g (100 mmol) of 55% m-chloro-perbenzoic acid are boiled under RF for 16 h in 200 ml of methylene chloride. Precipitation with 200 ml of diethyl ether gives 4-acetyl-pyridine N-oxide; m.p. 132°–133°.

Stage 1.2: 16.2 g (104.2 mmol) of 4-acetyl-2-chloro-pyridine are stirred at 110° with 116 ml of dimethylformamide diethylacetal for 1 h. Cooling to 0°, filtering and drying at 60° under HV give 3-dimethylamino-1-(2-chloro-4-pyridyl)-2-propen-1-one; $^1$H-NMR (dimethyl sulfoxide): 2.98 (3H,s), 3.2 (3H,s), 5.9 (1H,d), 7.8 (3H, m), 8.5 (1H Stage 1.3: 6.3 g (150 mmol) of cyanamide (50% in water) are added to a suspension of 16.1 g (100 mmol) of 3-trifluoromethyl-aniline in 35 ml of ethanol. 7.0 ml of nitric acid (65%, 0.1 mol) are then added to the brown solution and the reaction mixture is heated for 20 h under RF. It is then cooled to 0° and filtered, and the material retained on the filter is washed with ethanol and dried at 60° under HV to give 3-trifluoromethyl-phenylguanidine nitrate; $^1$H-NMR (dimethyl sulfoxide): 7.6 (7H,m), 9.9 (1H,br,s).

Stage 1.4: 150 mg (0.71 mmol) of 3-dimethylamino-1-(2-chloro-4-pyridyl)-2-propen-1-one are suspended in 1.5 ml of 2-propanol. 190 mg (0.712 mmol) of 3-trifluoromethylphenyl-guanidine nitrate and 31 mg (0.783 mmol) of sodium hydroxide are added and the reaction mixture is stirred for 18 h under RF. It is then cooled to RT and filtered, and the material retained on the filter is washed with 2-propanol and water and dried at 50° under HV to give N-(3-trifluoromethyl-phenyl)-4-(2-chloro-4-pyridyl)-2-pyrimidineamine;

m.p. 169°–171°, $R_f$=0.67 (methylene chloride:methanol=95:5), FAB-MS: 351 (M$^+$+H).

EXAMPLE 2

Analogously to Example 1, there is obtained from 20 mg (0.063 mmol) of N-(3-chloro-phenyl)-4-(2-chloro-4-pyridyl)-2-pyrimidineamine and 1 ml of 3-amino-1-propanol N-(3-chloro-phenyl)-4-[2-(3-hydroxy-propyl-amino)-4-pyridyl]-2-pyrimidineamine;

m.p. 144°–147°, $R_f$=0.12 (methylene chloride:methanol=95:5), FAB-MS: 356 (M$^+$+H).

The starting material is obtained in the following manner:

Stage 2.1: Analogously to Stage 1.4, there is obtained from 150 mg (0.7 mmol) of 3-dimethylamino-1-(2-chloro-4-pyridyl)-2-propen-1-one and 165 mg (0.71 mmol) of 3-chloro-phenyl-guanidine nitrate N-(3-chloro-phenyl)-4-(2-chloro-4-pyridyl)-2-pyrimidineamine;

m.p. 196°–198°, $R_f$=0.7 (methylene chloride:methanol=95:5).

Alternatively, N-(3-chloro-phenyl)-4-(2-chloro-4-pyridyl)-2-pyrimidineamine can be obtained in the following manner:

10.0 g (32 mmol) of N-(3-chloro-phenyl)-4-(N-oxido-4-pyridyl)-2-pyrimidineamine are stirred for 24 h in 100 ml of phosphorus oxychloride at 110°. The reaction mixture is stirred at 50° into 2N sodium hydroxide solution and extracted with tetrahydrofuran. Concentration and crystallisation (tetrahydrofuran/ethanol) of the residue give N-(3-chloro-phenyl)-4-(2-chloro4-pyridyl)-2-pyrimidineamine; m.p. 196°–198°, $R_f$=0.7 (methylene chloride:methanol=95:5).

The N-(3-chloro-phenyl)-4-(N-oxido-4-pyridyl)-2-pyrimidineamine used is prepared in the following manner:

10 g (35.4 mmol) of N-(3-chloro-phenyl)-4-(4-pyridyl)-2-pyrimidineamine and 11.1 g (35.4 mmol) of m-chloroperbenzoic acid are stirred for 5 h at RT in 500 ml of methylene chloride. Concentration and crystallisation (acetic acid) of the residue give N-(3-chloro-phenyl)-4-(N-oxido4-pyridyl)-2-pyrimidineamine; m.p. 274°–275°, $R_f$=0.6 (methylene chloride:methanol=9:1).

Stage 2.2: Analogously to Stage 1.3, there is obtained from 4.1 ml (0.04 mol) of 3-chloroaniline and 3.3 g (0.078 mol) of cyanamide (50% in water) 3-chloro-phenyl-guanidine nitrate; $^1$H-NMR (dimethyl sulfoxide): 7.2–7.7 (7H,m), 9.5 (1H,br,s).

EXAMPLE 3

The following compounds are prepared in a manner analogous to that described above and by simple conversion reactions, known per se, of the products:

a) N-(3-chloro-phenyl)-4-[2-(2-hydroxy-propyl-amino)-4-pyridyl]-2-pyrimidineamine, b) N-(3-chloro-phenyl)-4-[2-(2-carboxy-ethyl-amino)-4-pyridyl]-2-pyrimidineamine, c) N-(3-phenyl)-4-[2-(2-carbamoyl-ethyl-amino)-4-pyridyl]-2-pyrimidineamine, d) N-(3-chloro-phenyl)-4-[2-(2-ethoxycarbonylethylamino)-4-pyridyl]-2-pyrimidineamine, e) N-(3-trifluoromethyl-phenyl)-4-[2-(2-hydroxy-propyl-amino)-4-pyridyl]-2-pyrimidineamine, f) N-(3-trifluoromethyl-phenyl)-4-[2-(2-carboxy-ethyl-amino)-4-pyridyl]-2-pyrimidineamine, g) N-(3-trifluoromethyl-phenyl)-4-[2-(2-carbamoyl-ethyl-amino)-4-pyridyl]-2-pyrimidineamine, h) N-(3-trifluoromethyl-phenyl)-4-[2-(2-ethoxycarbonyl-ethyl-amino)-4-pyridyl]-2-pyrimidineamine, i) N-(3-chloro-phenyl)-4-[2-(2-imidazol-1-ylethyl-amino)-4-pyridyl]-2-pyrimidineamine, j) N-(3-chloro-phenyl)-4-[2-(2-acetamido-ethyl-amino)-4-pyridyl]-2-pyrimidineamine, k) N-(3-chloro-phenyl)-4-(2-hydrazino-4-pyridyl)-2-pyrimidineamine, l) N-(3-chloro-phenyl)-4-[2-(2-guanidyl-ethyl-amino)-4-pyridyl]-2-pyrimidineamine, m) N-(3-chloro-phenyl)-4-[2-{2-(methylamino-carbonylamino)-ethyl-amino}-4-pyridyl]-2-pyrimidineamine,
n) N-(3-chloro-phenyl)-4-[2-(2-amidino-ethyl-amino)-4-pyridyl]-2-pyrimidineamine,
o) N-(3-chloro-phenyl)-4-[2-(2-glycylamino-ethyl-amino)-4-pyridyl]-2-pyrimidineamine,
p) N-(3-chloro-phenyl)-4-[2-(N-{2-amino-ethyl}-aminocarbonyl)-4-pyridyl]-2-pyrimidineamine (see also Example 6),
q) N-(3-chloro-phenyl)-4-[2-(N-{2-hydroxy-ethyl}-aminocarbonyl)-4-pyridyl]-2-pyrimidineamine (see also Example 7),
r) N-(3-chloro-phenyl)-4-[2-(N-{3-amino-prop-1-yl}-aminocarbonyl)-4-pyridyl]-2-pyrimidineamine (see also Example 9),
s) N-(3-chloro-phenyl)-4-[2-(N-{3-hydroxy-propyl}-aminocarbonyl)-4-pyridyl]-2-pyrimidineamine (see also Example 8),
t) N-(3-chloro-phenyl)-4-[2-{2-(N-hydroxy-carbamoyl)-ethyl-amino}-4-pyridyl]-2-pyrimidineamine,
u) N-(3-chloro-phenyl)-4-[2-{3-(N-hydroxy-carbamoyl)-propyl-amino}-4-pyridyl]-2-pyrimidineamine,
v) N-(3-chloro-phenyl)-4-[2-{2-(dihydroxy-phosphoryloxy)-ethyl-amino}4-pyridyl]-2-pyrimidineamine,
w) N-(3-chloro-phenyl)-4-[2-{3-(dihydroxy-phosphoryloxy)-propyl-amino}-4-pyridyl]-2-pyrimidineamine,
x) N-(3-trifluoromethyl-phenyl)-4-[2-(2-{N-hydroxy-carbamoyl}-ethyl-amino)-4-pyridyl]-2-pyrimidineamine,
y) N-(3-trifluoromethyl-phenyl)-4-[2-(3-{N-hydroxy-carbamoyl}-propyl-amino)-4-pyridyl]-2-pyrimidineamine,
z) N-(3-trifluoromethyl-phenyl)-4-[2-(2-{dihydroxy-phosphoryl-oxy}-ethyl-amino)-4-pyridyl]-2-pyrimidineamine and
zα) N-(3-trifluoromethyl-phenyl)-4-[2-(3-{dihydroxy-phosphoryl-oxy}-propyl-amino)-4-pyridyl]-2-pyrimidineamine.

EXAMPLE 4

20 mg (0.063 mmol) of N-(3-chloro-phenyl)-4-(2-chloro-4-pyridyl)-2-pyrimidineamine are stirred for 26 h at 110° with 1 ml of ethylenediamine. Concentration and chromatography (methylene chloride:methanol:conc. ammonia solution=80:20: 1) give N-(3-chloro-phenyl)-4-[2-(2-amino-ethyl-amino)-4-pyridyl]-2-pyrimidineamine; $R_f$=0.15 (methylene chloride:methanol:conc. ammonia solution= 80:20:1), FAB-MS: 341 (M$^+$+1).

EXAMPLE 5

Analogously to Example 4, there is obtained from 50 mg (0.157 mmol) of N-(3-trifluoromethyl-phenyl)-4-(2-chloro-4-pyridyl)-2-pyrimidineamine and 1 ml of ethylenediamine N-(3-trifluoromethyl-phenyl)-4-[2-(2-amino-ethyl-amino)-4-pyridyl]-2-pyrimidineamine; $R_f$=0.15 (methylene chloride:methanol:conc. ammonia solution=80:20: 1), FAB-MS: 375 (M$^+$+H).

EXAMPLE 6

80 mg (0.24 mmol) of N-[3-chloro-phenyl]-4-(2-carboxy-4-pyridyl)-2-pyrimidineamine, 70.8 mg (0.36 mmol) of N-ethyl-N'-(3-dimethylaminopropyl)-carbodiimide hydrochloride and 42 mg (0.36 mmol) of N-hydroxysuccinimide are dissolved in 3 ml of dimethylformamide and stirred for 2.5 h at RT. The reaction mixture is then added dropwise at 0° within a period of 30 minutes to a solution of 0.77 ml (11.8 mmol) of ethylenediamine in 2 ml of DMF. After stirring for 14 h at RT, the reaction mixture is poured into 50 ml of ethyl acetate and extracted with 30 ml of water. The organic phase is dried (sodium sulfate) and concentrated. Crystallisation from isopropanol/ethanolic hydrochloric acid gives N-[3-chloro-phenyl]-4-[2-(N-{2-amino-ethyl}-aminocarbonyl)-4-pyridyl]-2-pyrimidineamine hydrochloride; m.p. 161°–163°, FAB-MS: 369 (M$^+$+H).

The starting material is obtained in the following manner:
Stage 6.1: 50 mg (0.16 mmol) of N-(3-chloro-phenyl)-4-(2-cyano-4-pyridyl)-2-pyrimidineamine are stirred in 5 ml of ethanol and 5 ml of 2N sodium hydroxide solution for 2 h at 60°. After cooling to RT and filtering, the material retained on the filter is washed with ethanol/water (9:1) and dried at 50° under HV to give the sodium salt of N-(3-chloro-phenyl)-4-(2-carboxy-4-pyridyl)-2-pyrimidineamine; m.p. >250°, $R_f$=<0.1 (methylene chloride:methanol=9:1).

EXAMPLE 7

Analogously to Example 6, them is obtained from 100 mg (0.3 mmol) of N-[3-chloro-phenyl]-4-(2-carboxy-4-pyridyl)-2-pyrimidineamine, 88.5 mg (0.46 mmol) of N-ethyl-N'-(3-dimethylaminopropyl)-carbodiimide hydrochloride, 53 mg (0.46 mmol) of N-hydroxysuccinimide and 0.9 ml (14 mmol) of ethanolamine N-[3-chloro-phenyl]-4-[2-(N-{2-hydroxy-ethyl}-aminocarbonyl)-4-pyridyl]-2-pyrimidineamine; m.p. 206°, FAB-MS: 370 (M$^+$+H).

EXAMPLE 8

Analogously to Example 6, there is obtained from 80 mg (0.24 mmol) of N-[3-chloro-phenyl]-4-(2-carboxy-4-pyridyl)-2-pyrimidineamine, 70 mg (0.36 mmol) of N-ethyl-N'-(3-dimethylaminopropyl)-carbodiimide hydrochloride, 42 mg (0.36 mmol) of N-hydroxysuccinimide and 0.7 ml (11.8 mmol) of aminopropanol N-[3-chloro-phenyl]-4-[2-(N-{3-hydroxy-propyl}-aminocarbonyl)-4-pyridyl]-2-pyrimidineamine;
m.p. 152°–153°, FAB-MS: 384 (M$^+$+H).

EXAMPLE 9

Analogously to Example 6, there is obtained from 50 mg (0.15 mmol) of N-[3-chloro-phenyl]-4-(2-carboxy-4-pyridyl)-2-pyrimidineamine, 44 mg (0.22 mmol) of N-ethyl—N'-(3-dimethylaminopropyl)-carbodiimide hydrochloride, 26 mg (0.22 mmol) of N-hydroxysuccinimide and 0.48 ml (7.3 mmol) of diaminopropane N-[3-chloro-phenyl]-4-[2-(N-{3-amino-prop-1-yl}-aminocarbonyl)-4-pyridyl]-2-pyrimidineamine hydrochloride; m.p. 173°–178°, FAB-MS: 383 (M$^+$+H).

EXAMPLE 10

Analogously to Example 1, there is obtained from 500 mg (1.5 mmol) of N-[3-chloro-phenyl]-4-(2-chloro-4-pyridyl)-2-pyrimidineamine and 1 ml (16.3 mmol) of aminoethanol N-[3-chloro-phenyl]-4-[2-(2-hydroxy-ethyl-amino)-4-pyridyl]-2-pyrimidineamine;
m.p. 180°–181°, FAB-MS: 342 (M$^+$+H).

EXAMPLE 11

Analogously to Example 1, there is obtained from 6.4 g (19.6 mmol) of N-[3-carboxy-phenyl]-4-(2-chloro-4-pyridyl)-2-pyrimidineamine and 12 ml (160 mmol) of 3-aminopropanol, after crystallisation from ethanol/1N hydrochloric acid, N-[3-carboxy-phenyl]-4-[2-(3-hydroxy-propyl-amino)-4-pyridyl]-2-pyrimidineamine;

m.p. 258°–259°, FAB-MS: 366 (M⁺+H).

The starting material is obtained in the following manner:

Stage 11.1: Analogously to Stage 1.3, there is obtained from 24.4 g (148 mmol) of amino-benzoic acid ethyl ester, 10.25 ml (150 mmol) of 65% nitric acid and 9.66 g (230 mmol) of 98% cyanamide 3-ethoxycarbonyl-phenyl-guanidine nitrate; ¹H-NMR (DMSO, D₂O): 1.3 (t,3H), 4.3 (q,2H), 7.4–7.9 (m,4H).

Stage 11.2: Analogously to Stage 1.4, there is obtained from 14.5 g (53.7 mmol) of 3-ethoxycarbonyl-phenyl-guanidine nitrate, 11.3 g (53.7 mmol) of 3-dimethylamino-1-(2-chloro-4-pyridyl)-2-propen-1-one and 2.4 g (60 mmol) of sodium hydroxide N-[3-ethoxy-carbonyl-phenyl]-4-(2-chloro-4-pyridyl)-2-pyrimidineamine; m.p. 149°–150°, FAB-MS: 355 (M⁺+H).

Stage 11.3: 9.4 g (26.5 mmol) of N-[3-ethoxycarbonyl-phenyl]-4-(2-chloro-4-pyridyl)-2-pyrimidineamine and 50 ml of 2N sodium hydroxide solution are boiled under RF in 300 ml of ethanol for 1 h. After cooling to RT, the reaction mixture is acidified (4N hydrochloric acid) and filtered. After drying at 50° under HV, lemon-yellow crystals of N-[3-carboxy-phenyl]-4-(2-chloro-4-pyridyl)-2-pyrimidineamine are obtained; m.p. 267°–268°, FAB-MS: 327 (M⁺+H).

EXAMPLE 12

2.0 g (5.4 mmol) of N-[3-carboxy-phenyl]-4-(2-(3-hydroxy-propyl-amino)-4-pyridyl)-2-pyrimidineamine and 0.28 ml (5.4 mmol) of conc. sulfuric acid are boiled under RF in 150 ml of methanol for 24 h. After cooling to RT, the reaction mixture is concentrated to half the volume, diluted with 100 ml of ethyl acetate and extracted twice with 50 ml of buffer (pH 7) each time. The organic phase is dried (Na₂SO₄) and concentrated. Crystallisation (methylene chloride/methanol) gives N-[3-methoxycarbonylphenyl]-4-[2-(3-hydroxy-propyl-amino)-4-pyridyl]-2-pyrimidineamine; m.p. 162°–163°, FAB-MS: 380 (M⁺+H).

EXAMPLE 13

Analogously to Example 1, there is obtained from 300 mg (0.95 mmol) of N-[3-chloro-phenyl]-4-(2-chloro-4-pyridyl)-2-pyrimidineamine and 3 ml (32.3 mmol) of aminobutanol N-[3-chloro-phenyl]-4-[2-(4-hydroxy-butyl-amino)-4-pyridyl]-2-pyrimidineamine;

m.p. 136°–139°, FAB-MS: 370 (M⁺+H).

EXAMPLE 14

Analogously to Example 1, there is obtained, in the melt, from 50 mg (0.16 mmol) of N-[3-chloro-phenyl]-4-(2-chloro-4-pyridyl)-2-pyrimidineamine and 350 mg (3.15 mmol) of histamine, that is to say 2-(imidazol-4-yl)-ethyl-amine, N-[3-chloro-phenyl]-4-{2-[2-(imidazol-4-yl)-ethyl-amino]-4-pyridyl}-2-pyrimidineamine;

m.p. 140°–146°, FAB-MS: 392 (M⁺+H).

EXAMPLE 15

Analogously to Example 1, there is obtained from 1.16 g (3.91 mmol) of N-[3-methyl-phenyl]-4-(2-chloro-4-pyridyl)-2-pyrimidineamine and 23 ml (304.9 mmol) of 3-aminopropanol N-[3-methyl-phenyl]-4-[2-(3-hydroxy-propyl-amino)-4-pyridyl]-2-pyrimidineamine; m.p. 138°–139°, FAB-MS: 336 (M⁺+H).

The starting material is obtained in the following manner:

Stage 15.1: Analogously to Stage 1.3, there is obtained from 2.02 ml (18.7 mmol) of m-toluidine, 1.95 ml (29.9 mmol) of conc. hydrochloric acid and 0.89 g (37.3 mmol) of 98% cyanamide, after precipitation with 0.47 g (37.3 mmol) of ammonium nitrate, 3-methyl-phenyl-guanidine nitrate; ¹H-NMR (DMSO): 2.3 (s,3H), 7.0–7.5 (m,8H), 9.5 (br, s, 1H).

Stage 15.2: Analogously to Stage 1.4, there is obtained from 1.09 g (5.17 mmol) of 3-methyl-phenyl-guanidine nitrate, 1.09 g (5.17 mmol) of 3-dimethylamino-1-(2-chloro-4-pyridyl)-2-propen-1-one and 0.23 g (5.68 mmol) of sodium hydroxide N-[3-methyl-phenyl]-4-(2-chloro-4-pyridyl)-2-pyrimidineamine; ¹H-NMR (DMSO): 2.3 (s,3H), 6.8 (d,1H), 7.2 (t, 1H), 7.6 (m,2H), 7.7 (s, 1H), 8.1 (m,1H), 8.2 (s, 1H), 8.6 (d, 1H), 8.7 (d,1H), 9.8 (s, 1H).

EXAMPLE 16

Analogously to Example 1, there is obtained from 168.8 mg (0.53 mmol) of N-[3-chloro-phenyl]-4-(2-chloro-4-pyridyl)-2-pyrimidineamine and 113.2 mg (1.06 mmol) of 5-aminopentanol N-[3-chloro-phenyl]-4-[2-(5-hydroxy-pentyl-amino)-4-pyridyl]-2-pyrimidineamine; FAB-MS: 384 (M⁺+H), 298.

EXAMPLE 17

500 mg (1.4 mmol) of N-[3-ethoxycarbonyl-phenyl]4-(2-chloro-4-pyridyl)-2-pyrimidineamine are stirred in 1 ml of 3-aminopropanol for 15 h at 140°. Chromatography (silica gel, methylene chloride:methanol=9:1) gives N-[3-{N-(3-hydroxy-propyl)-amino-carbonyl}-phenyl]-4-[2-(3-hydroxy-propyl-amino)-4-pyridyl]-2-pyrimidineamine;

m.p. 153°–154°, FAB-MS: 423 (M⁺+H).

EXAMPLE 18

100 mg (0.26 mmol) of N-[3-methoxycarbonyl-phenyl]-4-[2-(3-hydroxy-propyl-amino)-4-pyridyl]-2-pyrimidineamine and 0.5 ml of 1,3-diamino-propane are stirred for 24 h at 90° and then diluted with 20 ml of ethyl acetate and extracted with 2×10 ml of sodium chloride solution. The organic phase is dried, concentrated and crystallised from methylene chloride/diethyl ether to give N-[3-{N-(3-amino-propyl)-aminocarbonyl}-phenyl]-4-[2-(3-hydroxy-propyl-amino)-4-pyridyl]-2-pyrimidineamine;

m.p. 169°–170°, FAB-MS: 422 (M⁺+H).

EXAMPLE 19

Analogously to Example 18, there is obtained from 100 mg (0.26 mmol) of N-[3-methoxycarbonyl-phenyl]-4-[2-(3-hydroxy-propyl-amino)-4-pyridyl]-2-pyrimidineamine and 150 mg (1.35 mmol) of histamine, that is to say 2-(imidazol-4-yl)-ethyl-amine, N-[3-{N-(2-imidazol-4-yl-ethyl)-aminocarbonyl}-phenyl]-4-[2-(3-hydroxy-propylamino)-4-pyridyl]-2-pyrimidineamine; m.p. 181°–186°, FAB-MS: 459 (M⁺+H).

EXAMPLE 20

Analogously to Example 1, there is obtained from 300 mg (0.9 mmol) of N-[3-chloro-6-methyl-phenyl]-4-(2-chloro-4-pyridyl)-2-pyrimidineamine and 5.3 ml (70.65 mmol) of 3-aminopropanol N-[3-chloro-6-methyl-phenyl]-4-[2-(3-hydroxy-propylamino)-4-pyridyl]-2-pyrimidineamine; m.p. 117°–119°, FAB-MS: 370 (M⁺+H).

The starting material is obtained in the following manner:

Stage 20.1: Analogously to Stage 1.3, there is obtained from 10.0 g (60.62 mmol) of 5-chloro-2-methyl-aniline, 9.45 ml (113 mmol) of conc. hydrochloric acid and 5.94 g (141.2 mmol) of 98% cyanamide, after precipitation with 11.3 g (141.2 mmol) of ammonium nitrate, 5-chloro-2-methyl-phenyl-guanidine nitrate; $^1$H—NMR (DMSO): 2.2 (s,3H), 7.2–7.4 (m,7H).

Stage 20.2: Analogously to Stage 1.4, there is obtained from 1.75 g (7.12 mmol) of 3-chloro-6-methyl-phenyl-guanidine nitrate, 1.5 g (7.12 mmol) of 3-dimethylamino-1-(2-chloro-4-pyridyl)-2-propen-1-one and 0.31 g (7.83 mmol) of sodium hydroxide N-[3-chloro-6-methyl-phenyl]-4-(2-chloro-4-pyridyl)-2-pyrimidineamine; $^1$H-NMR (DMSO): 2.2 (s,3H), 7.1 (d×d, 1H), 73 (d,1H), 7.6 (d, 1H), 7.8 (d, 1H), 8.05 (d×d, 1H), 8.15 (s, 1H), 8.6 (m,2H), 9.2 (s, 1H).

EXAMPLE 21

Analogously to Example 1, there is obtained from 300 mg (0.85 mmol) of N-[3,6-dichloro-phenyl]-4-(2-chloro-4-pyridyl)-2-pyrimidineamine and 5.0 ml (66.55 mmol) of 3-aminopropanol N-[3,6-dichloro-phenyl]-4-[2-(3-hydroxy-propylamino)-4-pyridyl]-2-pyrimidineamine; m.p. 130°–132°, FAB-MS: 390 (M$^+$+H).

The starting material is obtained in the following manner:

Stage 21.1: Analogously to Stage 1.3, there is obtained from 10.0 g (61.72 mmol) of 2,5-dichloro-aniline, 8.25 ml (98.7 mmol) of conc. hydrochloric acid and 5.19 g (123.4 mmol) of 98% cyanamide, after precipitation with 9.88 g (123.4 mmol) of ammonium nitrate, 2,5-dichloro-phenyl-guanidine nitrate; $^1$H-NMR (DMSO): 7.4–7.7 (m,7H).

Stage 21.2: Analogously to Stage 1.4, there is obtained from 1.9 g (7.12 mmol) of 3,6-dichloro-phenyl-guanidine nitrate, 1.5 g (7.12 mmol) of 3-dimethylamino-1-(2-chloro-4-pyridyl)-2-propen-1-one and 0.31 g (7.83 mmol) of sodium hydroxide N-[3,6-dichloro-phenyl]-4-(2-chloro-4-pyridyl)-2-pyrimidineamine; $^1$H-NMR (DMSO): 7.25 (d×d, 1H), 7.6 (d,1H), 7.7 (d,1 H), 8.05 (m,2H), 8.2 (s,1H), 8.6 (d,1H), 8.7 (d, 1H), 9.25 (s, 1H).

EXAMPLE 22

Analogously to Example 1, there is obtained from 300 mg (0.86 mmol) of N-[3-chloro-6-methoxy-phenyl]-4-(2-chloro-4-pyridyl)-2-pyrimidineamine and 5.1 ml (67.4 mmol) of 3-aminopropanol N-[3-chloro-6-methoxy-phenyl]-4-[2-(3-hydroxy-propyl-amino)-4-pyridyl]-2-pyrimidineamine; m.p. 131°–133°, FAB-MS: 386 (M$^+$+H).

The starting material is obtained in the following manner:

Stage 22.1: Analogously to Stage 1.3, there is obtained from 10.0 g (63.45 mmol) of 5-chloro-2-methoxy-aniline, 8.5 ml (101.5 mmol) of conc. hydrochloric acid and 5.3 g (126.9 mmol) of 98% cyanamide, after precipitation with 10.2 g (126.9 mmol) of ammonium nitrate, 5-chloro-2-methoxy-phenyl-guanidine nitrate; $^1$H-NMR (DMSO): 3.9 (s,3H), 7.2–7.4 (m,7H).

Stage 22.2: Analogously to Stage 1.4, there is obtained from 1.87 g (7.12 mmol) of 3-chloro-6-methoxy-phenyl-guanidine nitrate, 1.5 g (7.12 mmol) of 3-dimethylamino-1-(2-chloro-4-pyridyl)-2-propen-1-one and 0.31 g (7.83 mmol) of sodium hydroxide N-[3-chloro-6-methoxy-phenyl]4-(2-chloro-4-pyridyl)-2-pyrimidineamine; $^1$H-NMR (DMSO): 3.9 (s,3H), 7.1 (d,1H), 7.7 (d,1H), 8.1 (d×d, 1H), 8.2 (s,1H), 8.3 (s,1H), 8.5 (s,1H), 8.6 (d1H), 8.75 (d,1H).

EXAMPLE 23

Analogously to Example 1, there is obtained from 100 mg (0.31 mmol) of N-[3-chloro-phenyl]-4-(2-chloro-4-pyridyl)-2-pyrimidineamine and 500 mg (5.63 mmol) of piperazine, from the melt after chromatography (methylene chloride:methanol=95:5), N-[3-chloro-phenyl]-4-[2-(1-piperazinyl)-4-pyridyl]-2-pyrimidineamine; m.p. 175°–180°, FAB-MS: 367 (M$^+$+H).

EXAMPLE 24

Analogously to Example 1, there is obtained from 100 mg (0.31 mmol) of N-[3-chloro-phenyl]-4-(2-chloro-4-pyridyl)-2-pyrimidineamine and 1.0 ml (7.5 mmol) of 4-(2-amino-ethyl)-morpholine N-[3-chloro-phenyl]-4-(2-[2-{4-morpholinyl}ethyl-amino]-4-pyridyl)-2-pyrimidineamine; m.p. 176°–186°, FAB-MS: 411 (M$^+$+H).

EXAMPLE 25

Analogously to Example 1, there is obtained from 100 mg (0.32 mmol) of N-[3-chloro-phenyl]-4-(2-chloro-4-pyridyl)-2-pyrimidineamine and 1.0 ml (7.4 mmol) of 1-(2-amino-ethyl)-piperazine N-[3-chloro-phenyl]-4-{2-[4-(2-amino-ethyl)-piperazin-1-yl)]-4-pyridyl}-2-pyrimidineamine; m.p. 250°, FAB-MS: 410 (M$^+$+H).

EXAMPLE 26

Analogously to Example 1, there is obtained from 100 mg (0.32 mmol) of N-[3-chloro-phenyl]-4-(2-chloro-4-pyridyl)-2-pyrimidineamine and 1.0 ml (8.35 mmol) of 2-(3-amino-propylamino)-ethanol N-[3-chloro-phenyl]-4-{2-[3-(2-hydroxy-ethyl-amino)-propylamino]-4-pyridyl}-2-pyrimidineamine; m.p. 143°–150°, FAB-MS: 399 (M$^+$+H).

EXAMPLE 27

Analogously to Example 1, there is unexpectedly obtained from 100 mg (0.315 mmol) of N-[3-chloro-phenyl]-4-(2-chloro-4-pyridyl)-2-pyrimidineamine and 1.0 ml (9.97 mmol) of 4-amino-morpholine N-[3-chloro-phenyl]-4-[2-(4-morpholinyl)-4-pyridyl]-2-pyrimidineamine; m.p. 163°–169°, FAB-MS: 368 (M$^+$+H).

EXAMPLE 28

Tablets each comprising 20 mg of active ingredient, for example one of the compounds of formula I described in Examples 1–27, are prepared with the following composition in customary manner:

| Composition: | |
|---|---|
| active ingredient | 20 mg |
| wheat starch | 60 mg |
| lactose | 50 mg |
| colloidal silica | 5 mg |
| talc | 9 mg |
| magnesium stearate | 1 mg |
| | 145 mg |

Preparation: The active ingredient is mixed with a portion of the wheat starch, with the lactose and with the colloidal silica, and the mixture is forced through a sieve. A further portion of the wheat starch is made into a paste with 5 times the amount of water on a water bath, and the powder mixture is kneaded with the paste until a slightly plastic mass has been formed.

The plastic mass is pressed through a sieve of approximately 3 mm mesh size and dried, and the resulting dry granules are forced through a sieve again. The remainder of the wheat starch, the talc and the magnesium stearate are admixed and the mixture is compressed to form tablets each weighing 145 mg and having a breaking notch.

EXAMPLE 29

Capsules each comprising 10 mg of active ingredient, for example one of the compounds of formula I described in Examples 1–27, are prepared in customary manner as follows:

| Composition: | |
|---|---|
| active ingredient | 2500 mg |
| talcum | 200 mg |
| colloidal silica | 50 mg |

Preparation: The active ingredient is intimately mixed with the talcum and the colloidal silica, and the mixture is forced through a sieve of 0.5 mm mesh size and introduced in 11-mg portions into hard gelatin capsules of suitable size.

What is claimed is:

1. An N-phenyl-2-pyrimidineamine derivative of formula I

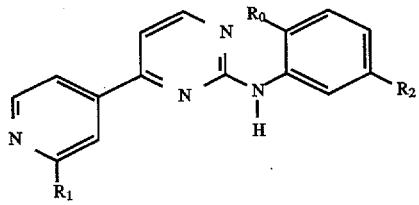

wherein
$R_0$ is hydrogen, halogen, lower alkoxy or lower alkyl,
$R_1$ is
 a) N-(amino-lower alkyl)-carbamoyl,
 b) N-(hydroxy-lower alkyl)-carbamoyl,
 c) hydrazino,
 d) cyclohexyl-amino that is unsubstituted or substituted by amino,
 e) piperazinyl that is unsubstituted or substituted by amino-lower alkyl,
 f) morpholinyl, or
 g) lower alkylamino that is substituted by morpholinyl, hydroxy-lower alkylamino, cyano, imidazolyl, guanidyl, amino, lower alkanoylamino, lower alkylamino-carbonylamino, amidino, di-lower alkylamino-cyclohexyl, carboxy, lower alkoxycarbonyl, carbamoyl, N-hydroxy-carbamoyl, hydroxy, lower alkoxy, dihydroxyphosphoryloxy, piperazinyl, lower alkanoyl-piperazinyl, formylpiperazinyl, prolylamido or by a radical of the formula $H_2N—CH(R)—C(=O)—NH—$ wherein R is hydrogen, $C_1$–$C_4$alkyl, benzyl, hydroxymethyl, 1-hydroxy-ethyl, mercaptomethyl, 2-methylthio-ethyl, indol-3-yl-methyl, phenyl-methyl, 4-hydroxy-phenyl-methyl, carbamoyl-methyl, 2-carbamoyl-ethyl, carboxy-methyl, 2-carboxy-ethyl, 4-amino-butyl, 3-guanidyl-propyl or R is 1H-imidazol-4-yl-methyl, and $R_2$ is $C_1$–$C_6$alkyl, $C_1$–$C_3$alkoxy, chlorine, bromine, iodine, trifluoromethyl, hydroxy, phenyl, amino, mono($C_1$–$C_3$alkyl)amino, di($C_1$–$C_3$alkyl)amino, $C_2$–$C_4$alkanoyl, propen-yloxy, carboxy, carboxymethoxy, ethoxycarbonyl-methoxy, sulfanilamido, N,N-di-($C_1$–$C_3$alkyl)sulfanilamido, N-methyl-piperazinyl, piperidinyl, 1H-imidazol-1-yl, 1H-triazol-1-yl, 1H-benzimidazol-2-yl, 1-naphthyl, cyclopentyl, 3,4-dimethyl-benzyl or a radical of one of the formulae:
—$CO_2R_3$, —NH—C(=O)—$R_3$, —N($R_3$)—C(=O)—$R_4$, —O—$(CH_2)_n$—N($R_3$)—$R_4$, —C(=O)—NH—$(CH_2)_n$—$R_4^a$, —C(=O)—NH—$(CH_2)_n$—N($R_3$)—$R_4$, —CH($CH_3$)—NH—CHO, —C($CH_3$)=N—OH, —C($CH_3$)=N—O—$CH_3$, —CH($CH_3$)—$NH_2$, —NH—$CH_2$—C(=O)—N($R_3$)—$R_4$,

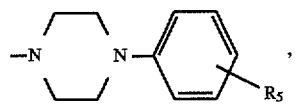

—$(CH_2)_m$—$R_6$, —X—$(CH_2)_m$—$R_6$ and

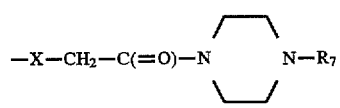

wherein $R_3$ and $R_4$ are each independently of the other $C_1$–$C_3$alkyl, $R_4^a$ is hydroxy, amino or imidazolyl, X is oxygen or sulfur, m is 1, 2 or 3, n is 2 or 3, $R_5$ is hydrogen, $C_1$–$C_3$alkyl, $C_1$–$C_3$alkoxy, chlorine, bromine, iodine or trifluoromethyl, $R_6$ is 1H-imidazol-1-yl or morpholinyl and $R_7$ is $C_1$–$C_3$alkyl or is phenyl that is unsubstituted or mono-substituted by $C_1$–$C_3$alkyl, halogen or by trifluoromethyl, or a salt thereof.

2. An N-phenyl-2-pyrimidineamine derivative according to claim 1 of formula Ia

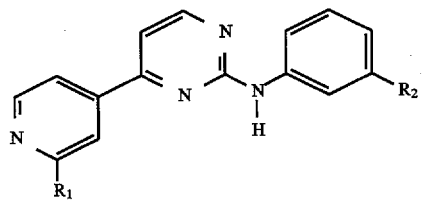

wherein
$R_1$ is
 a) N-(amino-lower alkyl)-carbamoyl,
 b) N-(hydroxy-lower alkyl)-carbamoyl,
 c) hydrazino,
 d) cyclohexyl-amino that is unsubstituted or substituted by amino, or
 e) lower alkylamino that is substituted by cyano, imidazolyl, guanidyl, amino, lower alkanoylamino, lower alkylamino-carbonylamino, amidino, di-lower alkylamino-cyclohexyl, carboxy, lower alkoxycarbonyl, carbamoyl, N-hydroxy-carbamoyl, hydroxy, lower alkoxy, dihydroxyphosphoryloxy, piperazinyl, lower alkanoyl-piperazinyl, formylpiperazinyl, prolylamido or by a radical of the formula $H_2N—CH(R)—C(=O)—NH—$ wherein R is hydrogen, $C_1$–$C_4$alkyl, benzyl, hydroxymethyl, 1-hydroxy-ethyl, mercaptomethyl, 2-methylthio-ethyl, indol-3-yl-methyl, phenyl-methyl, 4-hydroxy-phenyl-methyl, carbamoyl-methyl, 2-carbamoyl-ethyl, carboxy-methyl, 2-carboxy-ethyl, 4-amino-butyl, 3-guanidyl-propyl or R is 1H-imidazol-4-yl-methyl, and $R_2$ is $C_1$–$C_6$alkyl, $C_1$–$C_3$alkoxy, chlorine, bromine, iodine, trifluoromethyl, hydroxy, phenyl, amino, mono($C_1$–$C_3$alkyl)amino, di($C_1$–$C_3$alkyl)amino, $C_2-C_4$alkanoyl, prop-enyloxy, carboxy, carboxy-methoxy, ethoxycarbonyl-methoxy, sulfanilamido, N,N-di($C_1-C_3$alkyl)sulfanilamido, N-methyl-piperazinyl, piperidinyl, 1H-imidazol-1-yl, 1H-triazol-1-yl, 1H-benzimidazol-2-yl, 1-naphthyl, cyclopentyl, 3,4-dimethyl-benzyl or a radical of one of the formulae:
—$CO_2R_3$, —NH—C(=O)—$R_3$, —N($R_3$)—C(=O)—$R_4$, —O—$(CH_2)_n$—N($R_3$)—$R_4$, —C(=O)—NH—$(CH_2)_n$—N($R_3$)—$R_4$, —CH($CH_3$)—NH—CHO, —C($CH_3$)=N—OH, —C($CH_3$)=N—O—$CH_3$, —CH($CH_3$)—$NH_2$, —NH—$CH_2$—C(=O)—N($R_3$)—$R_4$,

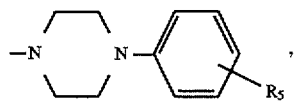

—$(CH_2)_m$—$R_6$, —X—$(CH_2)_m$—$R_6$ and

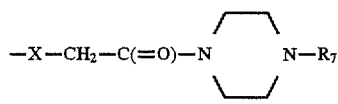

wherein $R_3$ and $R_4$ are each independently of the other $C_1-C_3$alkyl, X is oxygen or sulfur, m is 1, 2 or 3, n is 2 or 3, $R_5$ is hydrogen, $C_1-C_3$alkyl, $C_1-C_3$alkoxy, chlorine, bromine, iodine or trifluoromethyl, $R_6$ is 1H-imidazol-1-yl or morpholinyl and $R_7$ is $C_1-C_3$alkyl or is phenyl that is unsubstituted or mono-substituted by $C_1-C_3$alkyl, halogen or by trifluoromethyl, or a salt thereof.

3. A compound according to claim 1 of formula I, wherein $R_0$ is hydrogen, halogen, lower alkoxy or lower alkyl, $R_1$ is
a) N-(amino-lower alkyl)-carbamoyl,
b) N-(hydroxy-lower alkyl)-carbamoyl,
c) hydrazino,
d) piperazinyl that is unsubstituted or substituted by amino-lower alkyl,
e) morpholinyl, or
f) lower alkylamino that is substituted by morpholinyl, hydroxy-lower alkylamino, imidazolyl, guanidyl, amino, lower alkanoylamino, lower alkylamino-carbonylamino, amidino, carboxy, lower alkoxycarbonyl, carbamoyl, N-hydroxy-carbamoyl, hydroxy, dihydroxyphosphoryloxy or by a radical of the formula $H_2N$—CH(R)—C(=O)—NH— wherein R is hydrogen, and
$R_2$ is chlorine, trifluoromethyl, carboxy, a radical of the formula —$CO_2R_3$ wherein $R_3$ is $C_1-C_3$alkyl, or a radical of the formula —C(=O)—NH—$(CH_2)_n$—$R_4^a$ wherein n is 2 or 3 and $R_4^a$ is hydroxy, amino or imidazolyl, or a salt thereof.

4. A compound according to claim 1 of formula I, wherein $R_0$ is hydrogen,
$R_1$ is
a) N-(amino-lower alkyl)-carbamoyl,
b) N-(hydroxy-lower alkyl)-carbamoyl,
c) hydrazino or
d) lower alkylamino that is substituted by imidazolyl, guanidyl, amino, lower alkanoyl-amino, lower alkylamino-carbonylamino, amidino, carboxy, lower alkoxycarbonyl, carbamoyl, N-hydroxy-carbamoyl, hydroxy, dihydroxyphosphoryloxy or by a radical of the formula $H_2N$—CH(R)—C(=O)—NH— wherein R is hydrogen, and $R_2$ is chlorine or trifluoromethyl, or a salt thereof.

5. A compound according to claim 1 of formula I, wherein $R_0$ is hydrogen, chlorine, lower alkyl or lower alkoxy,
$R_1$ is N-(ω-amino-$C_2-C_3$alkyl)-carbamoyl, N-(ω-hydroxy-$C_2-C_3$alkyl)-carbamoyl, hydrazino, 2-hydroxy-propylamino or linear $C_2-C_3$alkylamino that is substituted in the ω-position by morpholinyl, ω-hydroxy-lower alkylamino, imidazolyl, guanidyl, amino, lower alkanoylamino, amidino, carboxy, lower alkoxycarbonyl, carbamoyl, N-hydroxycarbamoyl, hydroxy or by dihydroxyphosphoryloxy, and $R_2$ is chlorine, trifluoromethyl, carboxy, a radical of the formula —$CO_2R_3$ wherein $R_3$ is $C_1-C_3$alkyl, or a radical of the formula —C(=O)—NH—$(CH_2)_n$—$R_4^a$ wherein n is 2 or 3 and $R_4^a$ is hydroxy, amino or imidazolyl, or a salt thereof.

6. A compound according to claim 1 of formula I, wherein $R_0$ is hydrogen,
$R_1$ is N-(ω-amino-$C_2-C_3$alkyl)-carbamoyl, N-(ω-hydroxy-$C_2-C_3$alkyl)-carbamoyl, hydrazino, 2-hydroxy-propylamino or linear $C_2-C_3$alkylamino that is substituted in the ω-position by imidazolyl, guanidyl, amino, lower alkanoylamino, amidino, carboxy, lower alkoxycarbonyl, carbamoyl, N-hydroxy-carbamoyl, hydroxy or by dihydroxyphosphoryloxy, and $R_2$ is chlorine or trifluoromethyl, or a salt thereof.

7. A compound according to claim 1 of formula I, wherein $R_0$ is hydrogen, chlorine, methyl or methoxy,
$R_1$ is N-(ω-amino-$C_2-C_3$alkyl)-carbamoyl, N-(ω-hydroxy-$C_2-C_3$alkyl)-carbamoyl, hydrazino, 2-hydroxy-propylamino or linear $C_2-C_3$alkylamino that is substituted in the ω-position by 4-morpholinyl, ω-hydroxy-ethylamino, 1H-imidazol-1-yl, 1H-imidazol-4-yl, guanidyl, amino, acetylamino, amidino, carboxy, ethoxycarbonyl, carbamoyl, N-hydroxycarbamoyl, hydroxy or dihydroxyphosphoryloxy, and $R_2$ is chlorine, trifluoromethyl, carboxy, a radical of the formula —$CO_2R_3$ wherein $R_3$ is methyl, or a radical of the formula —C(=O)—NH—$(CH_2)_n$—$R_4^a$ wherein n is 2 or 3 and $R_4^a$ is hydroxy, amino or 1H-imidazol-4-yl, or a salt thereof.

8. N-(3-chloro-phenyl)-4-[2-(3-hydroxy-propyl-amino)-4-pyridyl]-2-pyrimidineamine or a pharmaceutically acceptable salt thereof according to claim 1.

9. A compound according to claim 1 of formula I or a pharmaceutically acceptable salt thereof, selected from N-(3-trifluoromethyl-phenyl)-4-[2-(3-hydroxy-propyl-amino)-4-pyridyl]-2-pyrimidineamine, N-(3-chloro-phenyl)-4-[2-(2-amino-ethyl-amino)-4-pyridyl]-2-pyrimidineamine, N-(3-trifluoromethyl-phenyl)-4-[2-(2-ammino-ethyl-amino)-4-pyridyl]-2-pyrimidineamine, N-[3-chloro-phenyl]-4-[2-(N-{2-amino-ethyl}-aminocarbonyl)-4-pyridyl]-2-pyrimidineamine, N-[3-chloro-phenyl]-4-[2-(N-{2-hydroxy-ethyl}-aminocarbonyl)-4-pyridyl]-2-pyrimidineamine N-[3-chloro-phenyl]-4-[2-(N-{3-hydroxy-propyl}-aminocarbonyl)-4-pyridyl]-2-pyrimidineamine, N-[3-chloro-phenyl]-4-[2-(N-{3-amino-prop-1-yl}-aminocarbonyl)-4-pyridyl]-2-pyrimidineamine, N-[3-chloro-phenyl]-4-[2-(2-hydroxy-ethyl-amino)-4-pyridyl]-2-pyrimidineamine, N-[3-carboxy-phenyl]-4-[2-(3-hydroxy-propyl-amino)-4-pyridyl]-2-pyrimidineamine, N-[3-methoxycarbonyl-phenyl]-4-[2-(3-hydroxy-propyl-amino)-4-pyridyl]-2-pyrimidineamine, N-[3-chloro-phenyl]-4-[2-(4-hydroxy-butyl-amino)-4-pyridyl]-2-pyrimidineamine, N-[3-chloro-phenyl]-4-{2-[2-(imidazol-4-yl)-ethyl-amino]-4-pyridyl}-2-pyrimidineamine, N-[3-methyl-phenyl]-4-[2-(3-hydroxy-propyl-amino)-4-pyridyl]-2-pyrimidineamine, N-[3-chloro-phenyl]-4-[2-(5-hydroxy-pentyl-amino)-4-pyridyl]-2-pyrimidineamine, N-[3-{N-(3-hydroxy-propyl) amino-carbonyl}-phenyl]-4-[2-(3-hydroxy-propyl-amino)-4-pyridyl]-2-pyrimidineamine, N-[3-{N-(3-amino-propyl)aminocarbonyl}-phenyl]-4-[2-(3-hydroxy-propyl-amino)-4-pyridyl]-2-pyrimidineamine, N-[3-{N-(2-imidazol-4-yl-ethyl)-aminocarbonyl}-phenyl]-4-[2-(3-hydroxy-propyl-amino)-4-pyridyl]-2-pyrimidineamine, N-[3-chloro-6-methyl-phenyl]-4-[2-(3-hydroxy-propyl-amino)-4-pyridyl]-2-pyrimidineamine, N-[3,6-dichloro-phenyl]-4-[2-(3-hydroxy-propyl-amino)-4-pyridyl]-2-pyrimidineamine, N-[3-chloro-6-methoxy-phenyl]-4-[2-(3-hydroxy-propyl-amino)-4-pyridyl]-2-pyrimidineamine, N-[3-chloro-phenyl]-4-[2-(1-piperazinyl)-4-pyridyl]-2-pyrimidineamine, N-[3-chloro-phenyl]-4-(2-[2-{4-morpholinyl}ethyl-amino]-4-pyridyl)-2-pyrimidineamine, N-[3-chloro-phenyl]-4-{2-[4-(2-amino-ethyl)-piperazin-1-yl)]-4-pyridyl}-2-pyrimidineamine, N-[3-chloro-phenyl]-4-{2-[3-(2-hydroxy-ethyl-amino)-propylamino]-4-pyridyl}-2-pyrimidineamine and N-[3-chloro-phenyl]-4-[2-(4-morpholinyl)-4-pyridyl]-2-pyrimidineamine and from the pharmaceutically acceptable salts thereof.

10. The N-phenyl-2-pyrimidine formula I according to claim 1 wherein said derivative comprises N-(3-chloro-phenyl)-4-[2-(2-carboxy-ethyl-amino)-4-pyridyl]-2-pyrimidineamine or a pharmaceutically acceptable salt of said derivative.

11. A process for the preparation of an N-phenyl-2-pyrimidineamine derivative of formula I

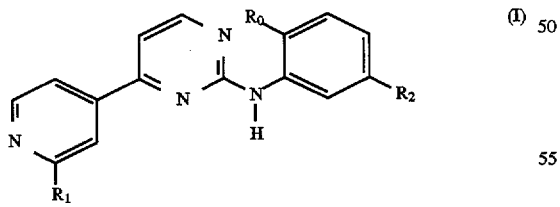

wherein $R_0$ is hydrogen, halogen, lower alkoxy or lower alkyl, $R_1$ is
a) hydrazino,
b) cyclohexyl-amino that is unsubstituted or substituted by amino, or
c) lower alkylamino substituted by morpholinyl, hydroxy-lower alkylamino, cyano, imidazolyl, guanidyl, amino, lower alkanoylamino, lower alkylamino-carbonylamino, amidino, di-lower alkylamino-cyclohexyl, carboxy, lower alkoxycarbonyl, carbamoyl, N-hydroxycarbamoyl, hydroxy, lower alkoxy, dihydroxyphosphoryloxy, piperazinyl, lower alkanoylpiperazinyl, formylpiperazinyl, protylamido or by a radical of the formula $H_2N$—$CH(R)$—$C(=O)$—$NH$— wherein R is hydrogen, $C_1$–$C_4$alkyl, benzyl, hydroxymethyl, 1-hydroxy-ethyl, mercaptomethyl, 2-methylthio-ethyl, indol-3-yl-methyl, phenyl-methyl, 4-hydroxy-phenyl-methyl, carbamoyl-methyl, 2-carbamoyl-ethyl, carboxy-methyl, 2-carboxy-ethyl, 4-amino-butyl, 3-guanidyl-propyl or R is 1H-imidazol-4-yl-methyl, and $R_2$ is $C_1$–$C_6$alkyl, $C_1$–$C_3$alkoxy, chlorine, bromine, iodine, trifluoromethyl, hydroxy, phenyl, amino, mono $(C_1$–$C_3$alkyl)amino, di$(C_1$–$C_3$alkyl)amino, $C_2$–$C_4$alkanoyl, propenyloxy, carboxy, carboxy-methoxy, ethoxycarbonyl-methoxy, sulfanilamido, N,N-di$(C_1$–$C_3$alkyl)sulfanilamido, N-methyl-piperazinyl, piperidinyl, 1H-imidazol-1-yl, 1H-triazol-1-yl, 1H-benzimidazol-2-yl, 1-naphthyl, cyclopentyl, 3,4-dimethyl-benzyl or a radical of one of the formula e:

—$CO_2R_3$, —$NH$—$C(=O)$—$R_3$, —$N(R_3)$—$C(=O)$—$R_4$, —$O$—$CH_2)_n$—$N(R_3)$—$R_4$, —$C(=O)$—$NH$—$(CH_2)_n$—$R_4{}^a$, —$C(=O)$—$NH$—$(CH_2)_n$—$R_3)$—$R_4$, —$CH(CH_3)$—$NH$—$CHO$, —$C(CH_3)$=$N$—$OH$, —$C(CH_3)$=$N$—$O$—$CH_3$, —$CH(CH_3)$—$N_2$, —$NH$—$CH_2$—$C(=O)$—$N(R_3)$—$R_4$,

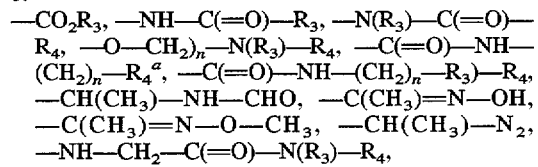

—$(CH_2)_m$—$R_6$, —$X$—$(CH_2)_m$—$R_6$ and

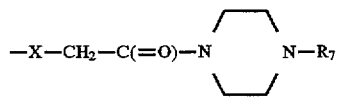

wherein $R_3$ and $R_4$ are each independently of the other $C_1$–$C_3$alkyl, $R_4{}^a$ is hydroxy, amino or imidazolyl, X is oxygen or sulfur, m is 1, 2 or 3, n is 2 or 3, $R_5$ is hydrogen, $C_1$–$C_3$alkyl, $C_1$–$C_3$alkoxy, chlorine, bromine, iodine or trifluoromethyl, $R_6$ is 1H-imidazol-1-yl or morpholinyl and $R_7$ is $C_1$–$C_3$alkyl or phenyl unsubstituted or mono-substituted by $C_1$–$C_3$alkyl, by halogen or by trifluoromethyl, or a salt thereof, wherein a) a compound of formula IV

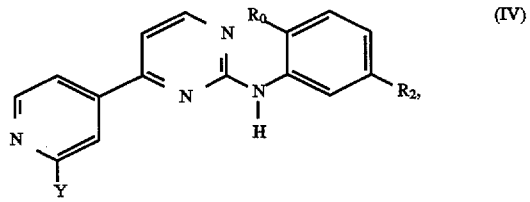

wherein Y is the group formed by having a hydroxy group esterified by a strong inorganic or organic acid and the functional groups present in the compound of formula IV, with the exception of the leaving group participating in the reaction, being, if necessary, in protected form, or a salt of the compound of formula IV, is reacted with an amine of formula V

H$_2$N—R$_{12}$ (V)

wherein R$_{12}$ is amino or unsubstituted or aminosubstituted cyclohexyl, or is lower alkyl that is substituted by morpholinyl, hydroxy-lower alkylamino, cyano, imidazolyl, guanidyl, amino, lower alkanoylamino, lower alkylaminocarbonylamino, amidino, di-lower alkylaminocyclo-hexyl, carboxy, lower alkoxycarbonyl, carbamoyl, N-hydroxy-carbamoyl, hydroxy, lower alkoxy, dihydroxyphosphoryloxy, piperazinyl, lower alkanoyl-piperazinyl, formylpiperazinyl, prolylamido or by a radical of the formula H$_2$N—CH(R)—C(=O)—NH— wherein R is hydrogen, C$_1$–C$_4$alkyl, benzyl, hydroxymethyl, 1-hydroxy-ethyl, mercaptomethyl, 2-methylthio-ethyl, indol-3-yl-methyl, phenyl-methyl, 4-hydroxy-phenyl-methyl, carbamoyl-methyl, 2-carbamoyl-ethyl, carboxy-methyl, 2-carboxy-ethyl, 4-amino-butyl, 3-guanidyl-propyl or R is 1H-imidazol-4-yl-methyl, the functional groups present in R$_{12}$ being, if necessary, in protected form; and removing the protecting groups, if present, to obtain the compound of formula I or the salt of the compound of formula I.

12. A process according to claim 11 for the preparation of a compound of formula Ia

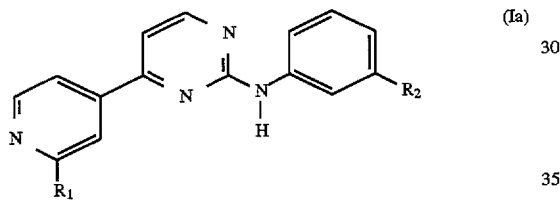
(Ia)

wherein

R$_1$ is
 a) hydrazino,
 b) cyclohexyl-amino that is unsubstituted or substituted by amino, or
 c) lower alkylamino that is substituted by cyano, imidazolyl, guanidyl, amino, lower alkanoylamino, lower alkylamino-carbonylamino, amidino, di-lower alkylamino-cyclohexyl, carboxy, lower alkoxycarbonyl, carbamoyl, N-hydroxy-carbamoyl, hydroxy, lower alkoxy, di-hydroxyphosphoryloxy, piperazinyl, lower alkanoyl-piperazinyl, formylpiperazinyl, propyl-amido or by a radical of the formula H$_2$N—CH(R)—C(=O)—NH— wherein R is hydrogen, C$_1$–C$_4$-alkyl, benzyl, hydroxymethyl, 1-hydroxy-ethyl, mercaptomethyl, 2-methylthio-ethyl, indol-3-yl-methyl, phenyl-methyl, 4-hydroxy-phenyl-methyl, carbamoyl-methyl, 2-carbamoyl-ethyl, carboxy-methyl, 2-carboxy-ethyl, 4-amino-butyl, 3-guanidyl-propyl or R is 1H-imidazol-4-yl-methyl, and R$_2$ is C$_1$–C$_6$alkyl, C$_1$–C$_3$alkoxy, chlorine, bromine, iodine, trifluoromethyl, hydroxy, phenyl, amino, mono (C$_1$–C$_3$alkyl)amino, di(C$_1$–C$_3$alkyl)amino, C$_2$–C$_4$alkanoyl, propenyloxy, carboxy, carboxymethoxy, ethoxycarbonyl-methoxy, sulfanilamido, N,N-di(C$_1$–C$_3$alkyl)sulfanilamido, N-methylpiperazinyl, piperidinyl, 1H-imidazol-1-yl, 1H-triazol-1-yl, 1H-benzimidazol-2-yl, 1-naphthyl, cyclopentyl, 3,4-dimethyl-benzyl or a radical of one of the formula e:

—CO$_2$R$_3$, —NH—C(=O)—R$_3$, —N(R$_3$)—C(=O)—R$_4$, —O—(CH$_2$)$_n$—N(R$_3$)—R$_4$, —C(=O)—NH—(CH$_2$)$_n$—N(R$_3$)—R$_4$, —CH(CH$_3$)—NH—CHO, —C(CH$_3$)=N—OH, —C(CH$_3$)=N—O—CH$_3$, —CH(CH$_3$)—NH$_2$, —NH—CH$_2$—C(=O)—N(R$_3$)—R$_4$,

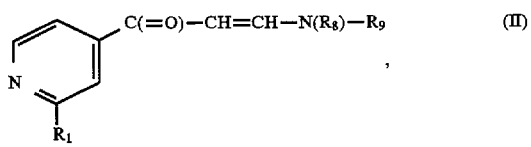

—(CH$_2$)$_m$—R$_6$, —X—(CH$_2$)$_m$—R$_6$ and

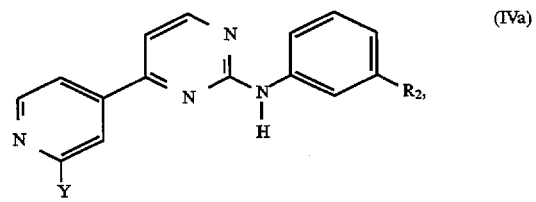

wherein R$_3$ and R$_4$ are each independently of the other C$_1$–C$_3$alkyl, X is oxygen or sulfur, m is 1, 2 or 3, n is 2 or 3, R$_5$ is hydrogen, C$_1$–C$_3$alkyl, C$_1$–C$_3$alkoxy, chlorine, bromine, iodine or trifluoromethyl, R$_6$ is 1H-imidazol-1-yl or morpholinyl, and R$_7$ is C$_1$–C$_3$alkyl or is phenyl that is unsubstituted or mono-substituted by C$_1$–C$_3$alkyl, halogen or by trifluoromethyl, or a salt thereof, wherein a) a compound of formula II

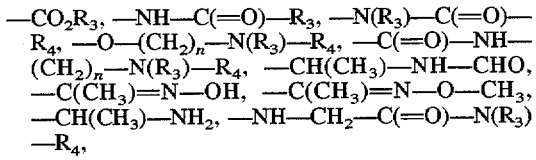 (II)

wherein R$_8$ and R$_9$ are each independently of the other lower alkyl and R$_1$ is as defined above, functional groups present in a compound of formula II, with the exception of the groups participating in the reaction, being, if necessary, in protected form, or a salt of such a compound is reacted with a compound of formula IIIa

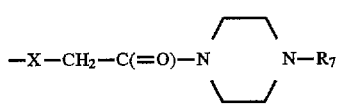 (IIIa)

wherein R$_2$ is as defined above, functional groups present in a compound of formula IIIa, with the exception of the guanidino group participating in the reaction, being, if necessary, in protected form, or with a salt of such a compound, and any protecting groups present are removed, or a compound of formula IVa

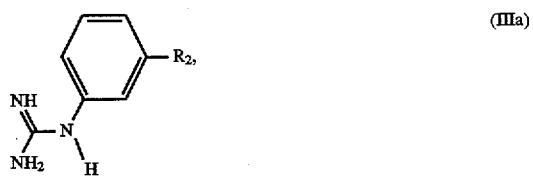 (IVa)

wherein Y is the group formed by having a hydroxy group esterified by a strong inorganic or organic acid and $R_2$ is as defined above, the functional groups present in the compound of formula IVa, with the exception of the leaving group participating in the reaction, being, if necessary, in protected form, or a salt of the compound of formula IVa is reacted with an amine of formula V

wherein $R_{12}$ is amino or unsubstituted or amino-substituted cyclohexyl, or is lower alkyl that is substituted by cyano, imidazolyl, guanidyl, amino, lower alkanoylamino, lower alkylaminocarbonylamino, amidino, di-lower alkylamino-cyclohexyl, carboxy, lower alkoxycarbonyl, carbamoyl, N-hydroxy-carbamoyl, hydroxy, lower alkoxy, dihydroxyphosphoryloxy, piperazinyl, lower alkanoyl-piperazinyl, formylpiperazinyl, prolylamido or by a radical of the formula $H_2N$—CH(R)—C(=O)—NH— wherein R is hydrogen, $C_1$-$C_4$alkyl, benzyl, hydroxymethyl, 1-hydroxy-ethyl, mercaptomethyl, 2-methylthio-ethyl, indol-3-yl-methyl, phenyl-methyl, 4-hydroxy-phenyl-methyl, carbamoyl-methyl, 2-carbamoyl-ethyl, carboxy-methyl, 2-carboxy-ethyl, 4-amino-butyl, 3-guanidyl-propyl or R is 1H-imidazol-4-yl-methyl, functional groups present in $R_{12}$ being, if necessary, in protected form, and removing the protecting groups, if present, to obtain the compound of formula I or the salt of the compound of formula I.

13. The process according to claim 11 wherein said process further comprises the step of treating the compound of formula I into the salt of the compound of formula I or the step of treating the salt of the compound of formula I into the compound of formula I.

14. The process according to claim 11 wherein said strong inorganic or organic acid is a hydrohalic acid.

15. The process according to claim 14 wherein said group formed by having a hydroxy group esterified by said hydrohalic acid is a halogen.

16. The process according to claim 15 wherein said halogen is chlorine.

17. A pharmaceutical composition comprising a compound of formula I according to claim 1 or a pharmaceutically acceptable salt of such a compound having at least one salt-forming group together with a pharmaceutical carried.

18. A pharmaceutical composition for the treatment of tumours in warm-blooded animals including humans, comprising a dose effective against a tumour of the bladder or skin of a compound of formula I according to claim 1, or a pharmaceutically acceptable salt of said compound having at least one salt-forming group, together with a pharmaceutical carrier.

19. The pharmaceutical composition of claim 11 comprising a dose of approximately 1 to 1000 mg of said compound of formula I per 70 kg of body weight.

20. The pharmaceutical composition of claim 11 comprising a dose of approximately 50 to 500 mg of said compound of formula I per 70 kg of body weight.

21. A method of treating a warm-blooded animal including a human, which comprises administering to a warm-blooded animal suffering from a tumour of the bladder or the skin a dose effective against said tumour of the bladder or skin of a compound of formula I according to claim 11, or of a pharmaceutically acceptable salt of said compound having at least one salt-forming group.

22. A pharmaceutical composition for the treatment of tumours in warm-blooded animals including humans, comprising a dose effective against epithelial carcinomas of a compound of formula I according to claim 1 or a pharmaceutically acceptable salt of said compound having at least one salt-forming group together with a pharmaceutical carrier.

23. A method of treating a warm-blooded animal including a human, which comprises administering to a warm-blooded animal suffering from an epithelial carcinoma disease a dose effective against said disease of a compound of formula I according to claim 1 or of a pharmaceutically acceptable salt of said compound having at least one salt-forming group.

* * * * *